US009696248B2

United States Patent
Scheucher

(10) Patent No.: US 9,696,248 B2
(45) Date of Patent: Jul. 4, 2017

(54) GAS INSULATED SWITCHGEAR MONITORING APPARATUS AND METHOD

(71) Applicant: Solon Manufacturing Company, Chardon, OH (US)

(72) Inventor: Karl Frederick Scheucher, Waite Hill, OH (US)

(73) Assignee: Solon Manufacturing Company, Chardon, OH (US)

( * ) Notice: Subject to any disclaimer, the term of this patent is extended or adjusted under 35 U.S.C. 154(b) by 204 days.

(21) Appl. No.: 14/700,066

(22) Filed: Apr. 29, 2015

(65) Prior Publication Data
US 2015/0308938 A1    Oct. 29, 2015

Related U.S. Application Data

(60) Provisional application No. 61/986,088, filed on Apr. 29, 2014, provisional application No. 62/103,958, filed on Jan. 15, 2015.

(51) Int. Cl.
*G01N 9/26*    (2006.01)
*G01N 33/00*    (2006.01)

(52) U.S. Cl.
CPC ......... *G01N 9/266* (2013.01); *G01N 33/0006* (2013.01)

(58) Field of Classification Search
CPC .......................... G01N 33/0006; G01N 9/266
See application file for complete search history.

(56) References Cited

U.S. PATENT DOCUMENTS 3,046,349 A    7/1962 Hicks
3,749,865 A    7/1973 Kalt et al.
(Continued)

FOREIGN PATENT DOCUMENTS

| CN | 1987412 A | 6/2007 |
|---|---|---|
| CN | 201653851 U | 11/2010 |
| WO | 2010/043268 A1 | 4/2010 |

OTHER PUBLICATIONS

International Search Report for Intl. App. No. PCT/US2016/013472, dated Apr. 29, 2016.
(Continued)

*Primary Examiner* — Francis Gray
(74) *Attorney, Agent, or Firm* — Baker & Hostetler LLP

(57) ABSTRACT

Mechanical, electronic, algorithmic, and computer network facets are combined to create a highly integrated advanced sensor that monitors the gas density, state-of-repair, and events associated with switchgear. Measurements of gas pressure, atmospheric pressure, gas temperature, are used with models of the non-ideal behavior of a particular gas to realistically estimate gas density. A hierarchical system of signal processing optimizes measurements working within high-frequency, real-time, short-term, medium-term, diurnal, long-term, and historical timeframes and overcomes measurement errors present in real-world applications. The time at which a condition such as gas density will reach a particular level is calculated. Events such as threshold attainments and switchgear operation are detected. A large memory stores all raw data values allowing flexible re-processing and verification at any future time. Instantaneous as well as logged information is communicated in convenient formats over a selected digital network. An embedded web server provides a familiar graphical user interface.

7 Claims, 29 Drawing Sheets

(56) References Cited

U.S. PATENT DOCUMENTS

| | | | |
|---|---|---|---|
| 4,364,271 | A | 12/1982 | Froome |
| 5,245,869 | A | 9/1993 | Clarke |
| 7,149,374 | B2 | 12/2006 | Lagakos et al. |
| 7,249,517 | B2 | 7/2007 | Heuer et al. |
| 9,212,966 | B2 | 12/2015 | Scheucher |
| 2010/0063749 | A1 | 3/2010 | Kurtz |
| 2012/0318044 | A1* | 12/2012 | Halbheer ............... G01N 9/26 73/30.02 |
| 2012/0329166 | A1 | 12/2012 | Skarping et al. |
| 2013/0031958 | A1* | 2/2013 | Scheucher ............ G01M 3/002 73/31.05 |
| 2014/0000342 | A1 | 1/2014 | Downie |
| 2014/0224770 | A1* | 8/2014 | Hensberger .............. G01N 9/36 218/52 |
| 2014/0326046 | A1* | 11/2014 | Zhang et al. ..... A61M 16/0003 73/31.04 |

OTHER PUBLICATIONS

United States Environmental Protection Agency, "Inventory of U.S. Greenhouse Gas Emissions and Sinks: 1990-2008", Washington, DC, Apr. 15, 2010, Available at http://www.epa.gov/climatechange/emissions/downloads10/US-GHG-Inventory-2010_Report.pdf.

Debra Knopman, Katie Smythe, "2004-2006 SF6 Data Summary", PM-2327-NEMA, Jun. 2007, Prepared for the National Electrical Manufacturers Association, Available at http://www.epa.gov/electricpower-sf6/documents/04-06_data_summary.pdf.

United States Environmental Protection Agency, "SF6 Emission Reduction Partnership for Electric Power Systems—2007 Annual Report", Washington, DC, Dec. 2008, Available at http://www.epa.gov/electricpower-sf6/documents/sf6_2007_ann_report.pdf.

Jos Olivier, Joost Bakker, Jan Willem Wouda, Rainer Bitsch, and Manfred Maiss, "Global Emission Sources of Greenhouse Gas Emissions from Industrial Processes: SF6", IPCC Task Force on National Greenhouse Gas Inventories, Jan. 2003, Available at <http://www.ipcc-nggip.iges.or.jp/public/gp/bgp/3_9_Global_Sources_Industrial_Processes_SF6.pdf.

L. G. Christophorou, J. K. Olthoff, and D. S. Green, "Gases for Electrical Insulation and Arc Interruption: Possible Present and Future Alternatives to Pure SF6", NIST Technical Note 1425, Nov. 1997, Available at <http://www.epa.gov/electricpower-sf6/documents/new_report_final.pdf.

United States Environmental Protection Agency, "Electric Transmission and Distribution Equipment Use—Final Rule: Mandatory Reporting of Greenhouse Gases (40 CFR 98, Subpart DD)", Nov. 2010, Available at <http://www.epa.gov/climatechange/emissions/downloads10/Subpart-DD_infosheet.pdf.

Alfieri, M. 2002. "Partner Case Study: Con Edison", Presented on behalf of Con Edison at the International Conference on SF6 and the Environment: Emission Reduction Strategies. San Diego, CA, Nov. 21-22, 2002. Available at <http://www.epa.gov/highgwp1/sf6/proceedings/agenda.html.

Robert Madding and Robert Benson, "Detecting SF6 Insulating Gas Leaks with an IR Imaging Camera", Electricity Today, pp. 12-15, Nov./Dec. 2007, Available at <http://www.electricity-today.com/et/issue0907/ir_camera.pdf.

Jan-Martin Rhiemenier, Sina Wartmann, Marcello Pagnotta, Natalia Makowska, and Xingyu Li, "Update on global SF6 Emissions trends from electrical equipment—Edition 1.1", Ecofys Germany GmbH, Jul. 2010, Available at <http://www.ecofys.com/com/publications/brochures_newsletters/documents/ESI-SF6_Finalreport_edition11_100701_v01.pdf.

U.S. Department of Energy, "U.S. Energy Information Administration Electric Power Annual 2009", Washington, DC, Nov. 2010, Available at <http://www.eia.gov/cneaf/electricity/epa/epa_sum.html>.

Wika Alexander Wiegand GmbH & Co. KG, "Gas Density Monitor (GDM) with Integrated Gas Density Transmitter, Model 233.52.100 TI", Klingenberg, Germany, May 2009, Available at <http://en-co.wika.de/upload/DS_SP6005_GB_7922.PDF.

J. Blackman, M. Averyt, and Z. Taylor, "SF6 Leak Rates from High Voltage Circuit Breakers—U.S. EPA Investigates Potential Greenhouse Gas Emissions Source", presented at the International Conference on SF6 and the Environment: Electric Power Systems—Partnership Update, Nov. 28, 2006, Available at <http://www.epa.gov/electricpower-sf6/documents/leakrates_circuitbreakers.pdf.

General Electric Company, "72.5kV Circuit Breakers Data Sheet", Nov. 10, 1999, Available at <http://www.geindustrial.com/publibrary/checkout/72.5DAT?TNR=Data%20Sheets|72.5DAT|PDF.

General Electric Company, "121kV Circuit Breakers Data Sheet", Mar. 1, 2002, Available at <http://www.geindustrial.com/publibrary/checkout/121DATA?TNR=Data%20Sheets|121DATA|PDF.

General Electric Company, "145kV Circuit Breakers Data Sheet", Nov. 10, 1999, Available at <http://www.geindustrial.com/publibrary/checkout/Data%20Sheets|145DATA|PDF.

General Electric Company, "169kV Circuit Breakers Data Sheet", Nov. 10, 1999, Available at <http://www.geindustrial.com/publibrary/checkout/Data%20Sheets|169DATA|PDF.

General Electric Company, "242kV Circuit Breakers Data Sheet", Nov. 10, 1999, Available at <http://www.geindustrial.com/publibrary/checkout/Data%20Sheets|242DATA|PDF.

General Electric Company, "362kV Circuit Breakers Data Sheet", Nov. 10, 1999, Available at <http://www.geindustrial.com/publibrary/checkout/Data%20Sheets|362DATA5|PDF.

General Electric Company, "550kV Circuit Breakers Data Sheet", Nov. 10, 1999, Available at <http://www.geindustrial.com/publibrary/checkout/Data%20Sheets|550DATA4|PDF.

Solon Manufacturing Company, "2TC, SF Gas Density Switch, Intrinsic Gauge Design", Chardon, OH, Available at <http://www.solonmfg.com/controls/techdocs/documents/2tcspec.pdf.

Giancarlo Scalabrin, Luigi Bettio, Paolo Marchi, and Paolo Stringari, "A Fundamental Equation of State for Sulfur Hexafluoride (SF6) in Extended Equation of State Format", JPCRD 36(2) pp. 617-662, 2007, Available at <http://energyfromthorium.com/forum/download/file.php?id=44&sid=275692ae3353e590221e1226f0501ac1.

Maryland Department of the Environment, "Maryland CO2 Budget Trading Program, COMAR 26.09.03", Baltimore, MD, Aug. 2009, Available at <http://www.mde.state.md.us/programs/Air/RGGI/Documents/www.mde.state.md.us/assets/document/air/RGGI/04_SF6_Offset_FINAL.pdf.

California Environmental Protection Agency, Air Resources Board, "Proposed Regulation Order: Regulation for Reducing Sulfur Hexafluoride Emissions from Gas Insulated Switchgear", Sacramento, CA, Jan. 7, 2010, Available at <http://www.arb.ca.gov/regact/2010/sf6elec/appa.pdf.

United Nations Framework Convention on Climate Change, "SF6 Emission Reductions in Electrical Grids", Bonn, Germany, Sep. 29, 2006, Available at <http://cdm.unfccc.int/filestorage/CDMWF_AM_5WABP18CK9HOSTV8E9CKDPFZM7UKQU/EB26_repan02_AM0035_NM0135.pdf?t=ekZ8MTI5MTM5NDM5NS45NA==|3FfpdD3n1BJADrv6dXLw5eW37cE=.

United States Department of the Interior Bureau of Reclamation, "Management and Safe Handling Procedures for Sulfur Hexaflouride (SF6) Gas", Mar. 2004, Available at <http://www.usbr.gov/power/data/fist/fist5$_{13}$9/fist5_9.pdf.

\* cited by examiner

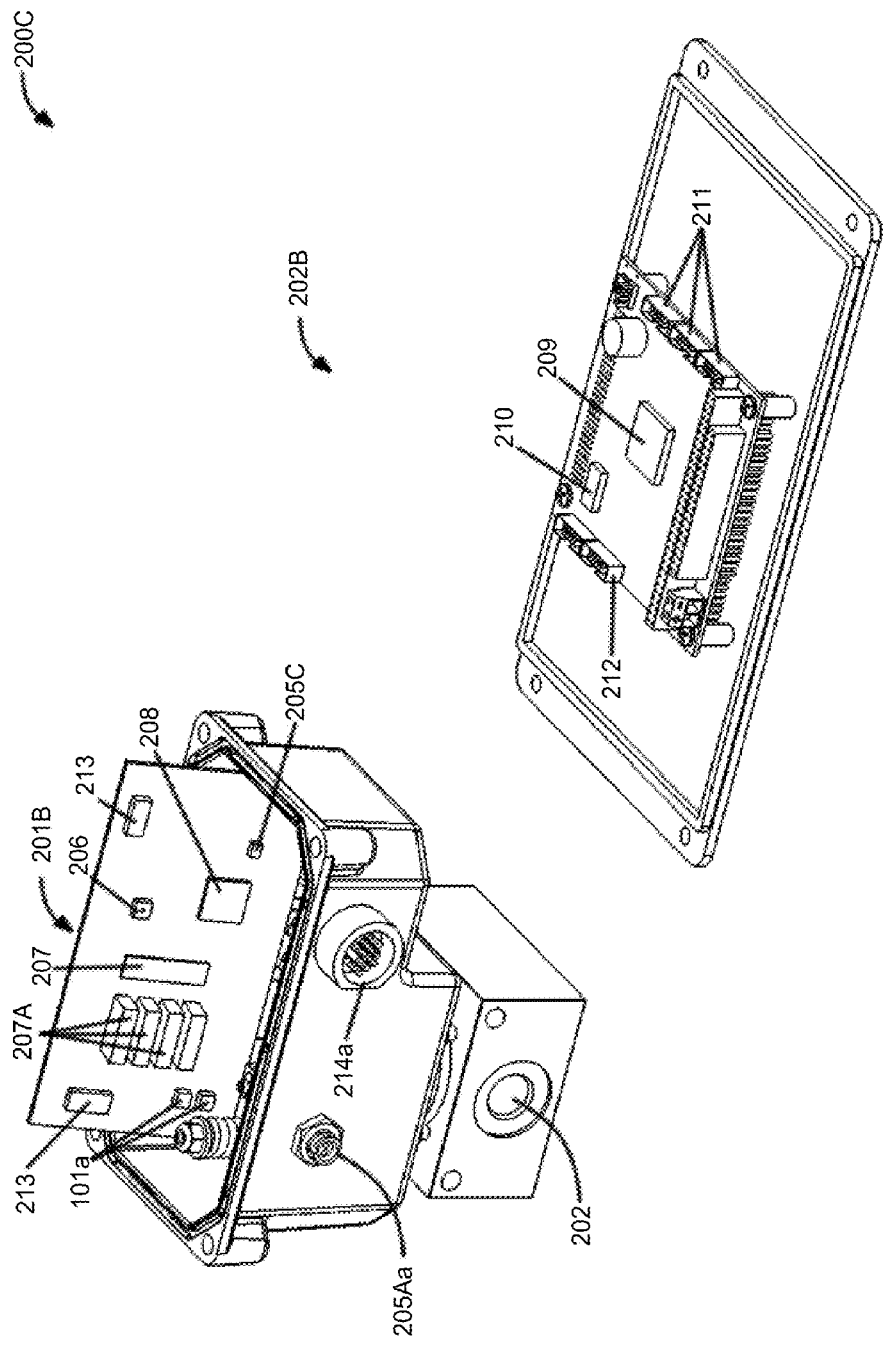

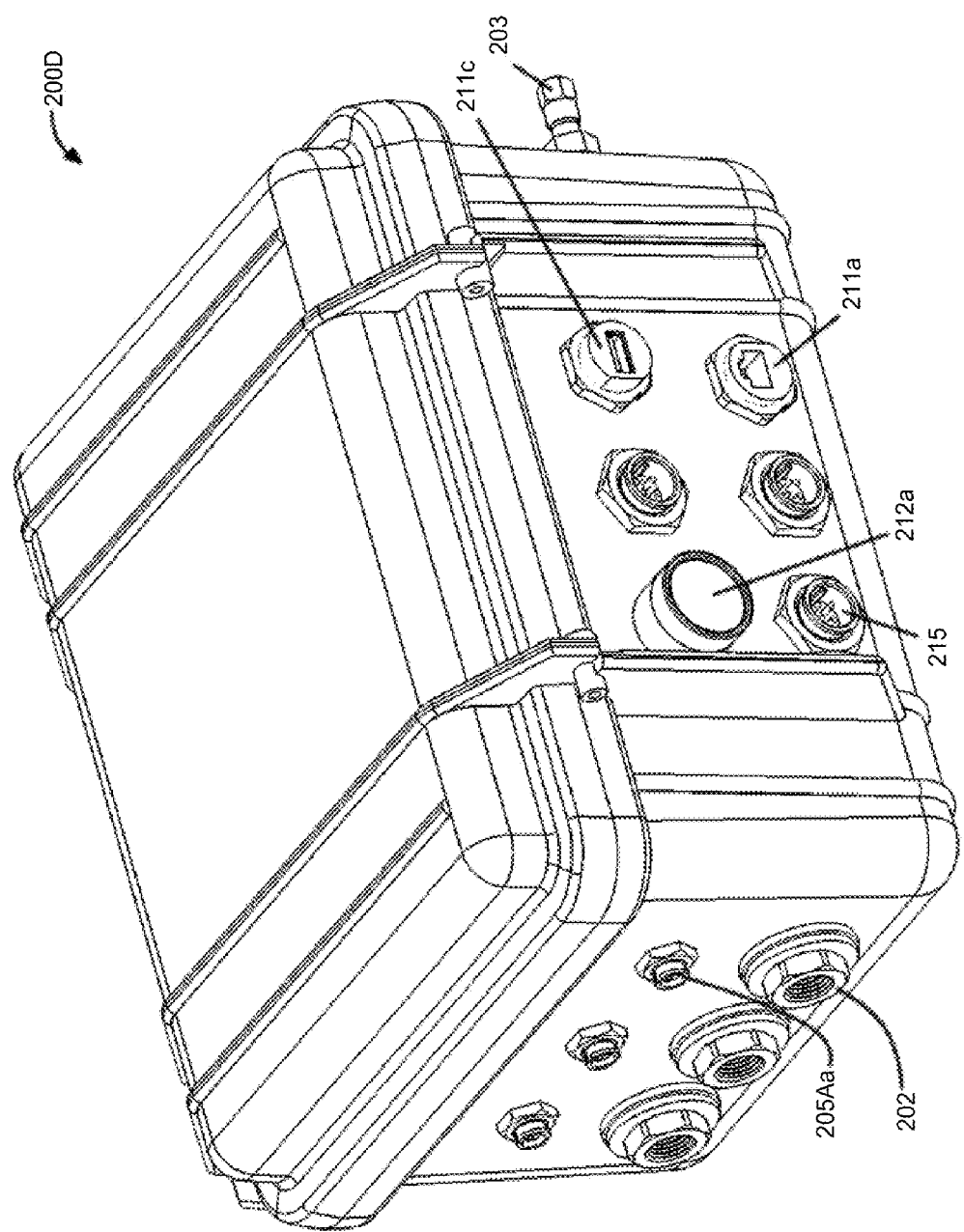

GAS INSULATED SWITCHGEAR MONITORING APPARATUS AND METHOD

This application claims priority to, and the benefit of U.S. Provisional patent application Ser. No. 61/986,088 filed Apr. 29, 2014 which is incorporated herein by reference hereto in its entirety. The application claims priority to, and the benefit of U.S. Provisional patent application Ser. No. 62/103,958 filed Jan. 15, 2015 which is incorporated herein by reference hereto in its entirety.

FIELD OF THE INVENTION

The field of invention is the field of intelligent gas sensors with the capability to effectively measure the pressure and temperature of gas contained in a fixed volume, to estimate the gas density, and to track changes in density that occur as a result of additions or losses of gas. The invention is also in the field of intelligent, networked sensors that exchange sensor measurements and sensor configuration and control information over communication networks. The field of invention also includes sensors that measure time-varying environmental conditions such as ambient temperature, atmospheric pressure, ambient light conditions, ambient sound levels, and electrical conditions including AC and DC voltages and currents. The invention also comprises the field of dielectric gas sensors and gas leakage sensors. All of the above applications are of interest in the management and operation of high voltage switchgear used in the electric utility and related industries.

BACKGROUND OF THE INVENTION

There is a clear need for monitoring dielectric gases and gas mixtures used for insulation and are suppression in high voltage switchgear used throughout the electric utility and related industries. Prescribed levels of gas are required for safe operation of this equipment. A decline in gas level due to gas leakage or other losses must be detected and maintenance activities must be scheduled to restore gas levels or else unsafe conditions or catastrophic equipment failure may result. There are a variety of products commonly called density monitors that have been used by the industry to detect low density levels and provide a system level alarm when gas replenishment is needed. These density monitors typically provide a second level of alarm when gas levels become so low that safe operation of the switchgear is not possible. These density monitor type products are inherently low resolution sensors signaling only a few different level conditions (such as "alarm level" and "lockout level"). Unfortunately, they do not provide the information needed to enable operators to fine tune maintenance and repair schedules and minimize associated operating costs. Further, the environmental cost of gases leaked from such switchgear can be severe. For example, sulfur hexafluoride gas ($SF_6$) is a dielectric gas of choice in widespread use in the industry and is a potent greenhouse gas (GWP 23,900 times that of CO2). The two-level density monitor type products are lacking when it comes to early detection and mitigation of environmentally harmful gas leaks. A gas monitoring system featuring high resolution density measurement and changing density level prediction is a valuable tool for reducing high-voltage switchgear maintenance and repair costs and for detecting gas leaks that pose a danger to the environment. This invention is such a high resolution gas monitoring system that provides these valuable benefits.

Gas density estimates are known to be derivable in a straight-forward fashion from the absolute temperature and the absolute pressure of a gas in a fixed volume using the ideal gas law wherein the density is predicted to be simply proportional to the pressure and inversely proportional to the temperature:

$$pV = nRT \therefore \frac{n}{V} = \frac{p}{RT} \tag{1}$$

where p is absolute pressure, V is volume, n is the gas mass, T is the absolute temperature, and R is the coefficient of proportionality (often referred to as the ideal gas constant).

It is well known that real world gases behave in a way that is more or less non-ideal as the density and temperature of the gas varies. It has been found that a better estimate of the state of a real world gas is available using the so-called virial equation of state:

$$\frac{pV}{nRT} = 1 + B(T)\frac{n}{V} + C(T)\frac{n^2}{V^2} + \ldots \tag{2}$$

The coefficients B(T), C(T), etc. are the so-called first order, second order, etc. virial coefficients respectively and depend upon temperature in a way peculiar to each particular gas or gas mixture. Accurate determination of the absolute pressure and absolute temperature of the monitored gas is still prerequisite to using the virial equation of state to accurately estimate its density.

When a gas sensor is utilized to estimate the gas density in a fixed volume tank of an outdoor high-voltage breaker, the temperatures measured by the gas sensor and the effective temperature of the gas within the tank often diverge significantly over the course of the day (see FIG. 5). For example, over the course of a 180-day test period with a gas sensor applied to a particular high voltage breaker charged with $SF_6$, temperature discrepancies between the sensor temperature measurement and different points on the gas tank ranged from −5.2° C. to +7.9° C. The discrepancy is even larger because the temperature of the gas at different points inside the tank is known to vary even further. Significant temperature gradients arise due to asymmetric heating or cooling due to differential exposure to wind, sun, and precipitation. Localized heating of gas near conductors and contacts carrying variable electrical currents within the tank of electrical equipment is another source of temperature disequilibrium. There is no simple method by which a temperature probe may be positioned so as to measure a temperature that reliably accurately reflects the effective ensemble temperature within a tank, effective ensemble temperature meaning the temperature value that would be observed if the gas system were allowed to come to thermal equilibrium. In the example above, the temperature discrepancies, if unaccounted, lead to density estimate errors ranging from −1.62 to +0.90 $kg/m^3$. Given that the typical operating densities for switchgear charged with SF6 are in the 40 $kg/m^3$ range, the inaccuracy represents a significant percentage error. Accurate gas pressure measurement, while non-trivial, is relatively straight-forward. To summarize, when the effective gas temperature is above the sensor measured temperature (which often arises when the ambient temperature is falling) the density is estimated to be higher than actual. Conversely, when the tank temperature is below the sensor temperature (when ambient temperature is rising typically) the density is estimated to be lower than actual. An example depicting this phenomenon is shown in FIG. 5 and described below.

SUMMARY OF THE INVENTION

The apparatus of the present invention (of the "system") is installed, either permanently or temporarily, to a gas tank of a high-voltage breaker or similar switchgear. Controllers integral to the system operate an array of sensors acquiring real-time information that is processed with specific algorithms to yield gas density estimates. The real-time sensor information is logged into a database. A nonvolatile memory used to store the database is sufficiently large and holds real-time sensor information (for example, acquired every second or faster) corresponding to a long period of operation (for example several years or longer). The information in the database is used for various analyses of switchgear events in timeframes ranging from long-term gas density changes to high-speed events such as breaker switching operation to short-term phenomenon such as dissipative heating of the gas within a tank due to contact or conductor resistance under current loads (FIG. 1).

The apparatus includes controllers operating sensors used to measure gas pressure, atmospheric pressure, temperature at one or more points on the surface of a gas tank, and temperatures at the pressure sensor and other locations within the apparatus. The temperature sensor may be of any type including thermistors, thermocouples, RTD, silicon, or other well known types. The pressure sensors may also be of any type.

The controller also monitors system variables in real-time including supply and reference voltage levels. A real-time clock with millisecond resolution is used as a time base for acquiring and logging all of the above-mentioned real-time data into the database.

The controller may comprise one or more physically distinct processors distributed at locations within the apparatus in a way that optimizes signal integrity and system performance. When distributed processors are employed, a network is employed enabling information to be communicated between processors. A user interface is always employed allowing information to be easily communicated between the controller and the user.

Real-time information that is acquired and logged into the database is input to the signal processing algorithms of the present invention. These algorithms may be divided into several categories based upon the timeframe in which each operates:

a) high-frequency
b) real time (approximately 1 second)
c) short-term (approximately 5-minute)
d) medium-term or diurnal (approximately daily)
e) long-term (approximately 30-day), and
f) historical timeframes It is an objective of the present invention to determine the temperature at one or more locations associated with the gas within a tank and to use specific algorithms operating on these location temperatures and other information to infer a temperature that is representative of the effective, absolute, ensemble temperature of the gas within the tank.

It is an objective of the present invention to determine the pressure relative to atmosphere of the gas within a tank.

It is an objective of the present invention to determine the atmospheric pressure.

It is an objective of the present invention to determine the absolute pressure of the gas within a tank.

It is an objective of the present invention to utilize absolute pressure and absolute temperature information to estimate the density of a specific type of gas within a tank.

Objectives of the present invention also include:

1) provide a reliable estimate of gas density during periods of relatively constant, slow leak or slow fill conditions
2) detect fast changes in density such as during fast fill or gas removal and adapt the density estimate accordingly
3) provide a meaningful confidence level for the current density estimate
4) track and trend the density over longer periods and report the information in understandable formats
5) given current density trends, estimate time to thresholds such as alarm and lockout that converge as expected
6) estimate annual gas loss as a percentage of nameplate capacity
7) log gas fills and losses and report same in a simple, ongoing log
8) display real time temperature corrected pressure as it would be reported by an electromechanical mechanism without signal processing, the expected response of a mechanical gauge and of switch contacts responding to temperatures which may be different than the effective gas temperature
9) provide processed and real time data in a way that is conducive to subsequent processing and analyses
10) capture and analyze high-frequency vibration information stemming from breaker operation, compressor operation, and other ambient vibration events such as technician activity, thunder, wind, etc.

It is an objective of the present invention to use density estimates and pressure measurements to deduce the effective temperature of gas internal to the tanks or compartments of high-voltage switchgear.

It is an objective of the present invention to utilize the inferred temperature rise of the dielectric gas in high-voltage switchgear to deduce changes in contact resistance that are indicative of the state of repair of the switchgear.

It is an objective of the present invention to communicate information to a SCADA (System Control and Data Acquisition) network.

It is an objective of the present invention to incorporate a web server providing a graphical user interface for users to access information using any web browser running on any hardware platform over a wired or wireless network.

Although this patent application emphasizes use of the present invention for sensing $SF_6$ in high-voltage switchgear applications, it is an important goal of the invention to be readily adaptable to many different gases and gas mixtures used in a broad range of processes.

BRIEF DESCRIPTION OF THE DRAWINGS

FIG. 2C is a view of the circuit board assemblies of the first embodiment.

FIG. 2D is a perspective view of a second embodiment of the apparatus.

DESCRIPTION OF THE INVENTION

Figure 1:
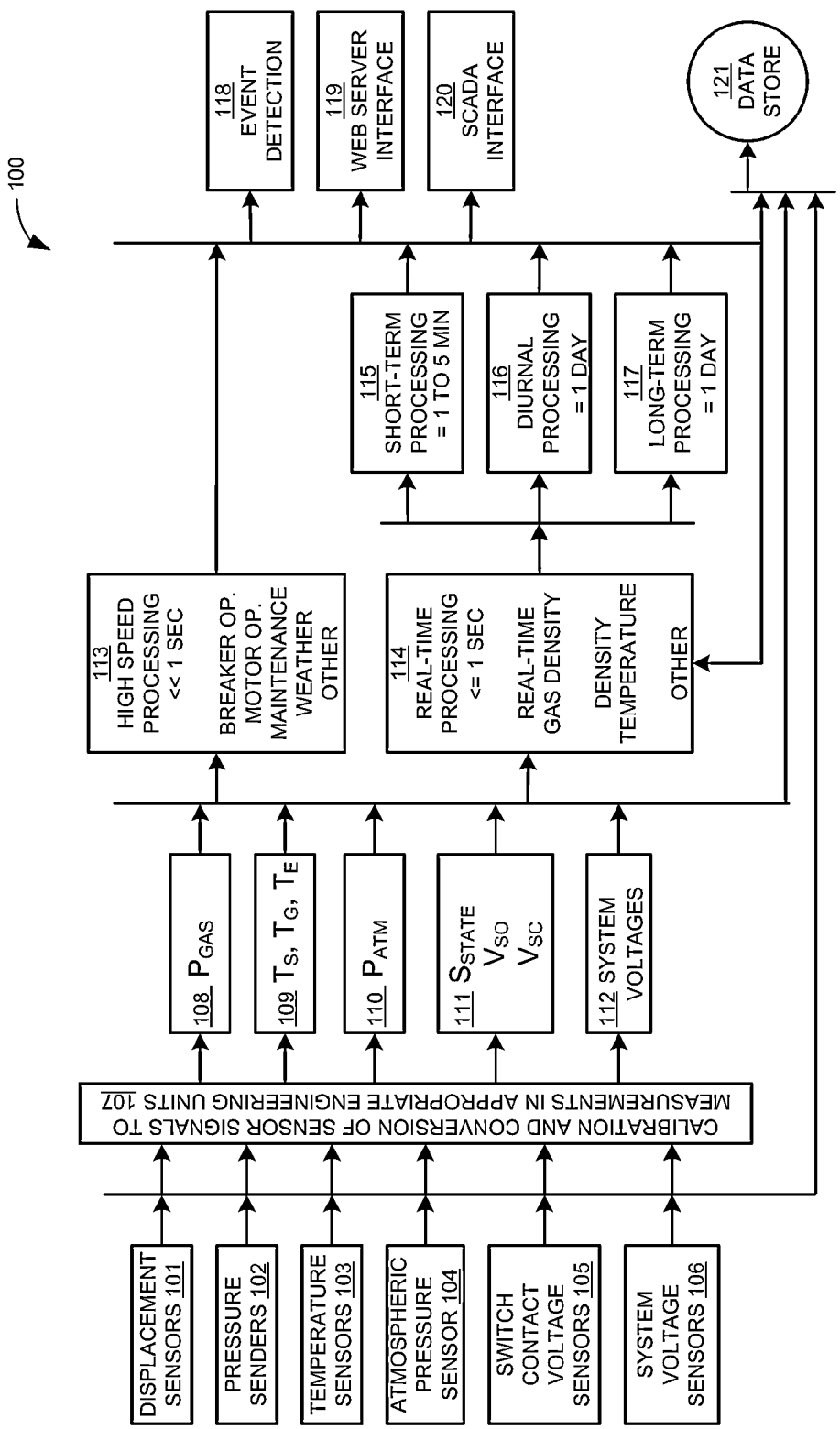
FIG. 1 is a high-level block diagram of the signal processing system.

FIG. 1 is a high level block diagram 100 of the signal processing performed in the present invention.

Figure 2A:
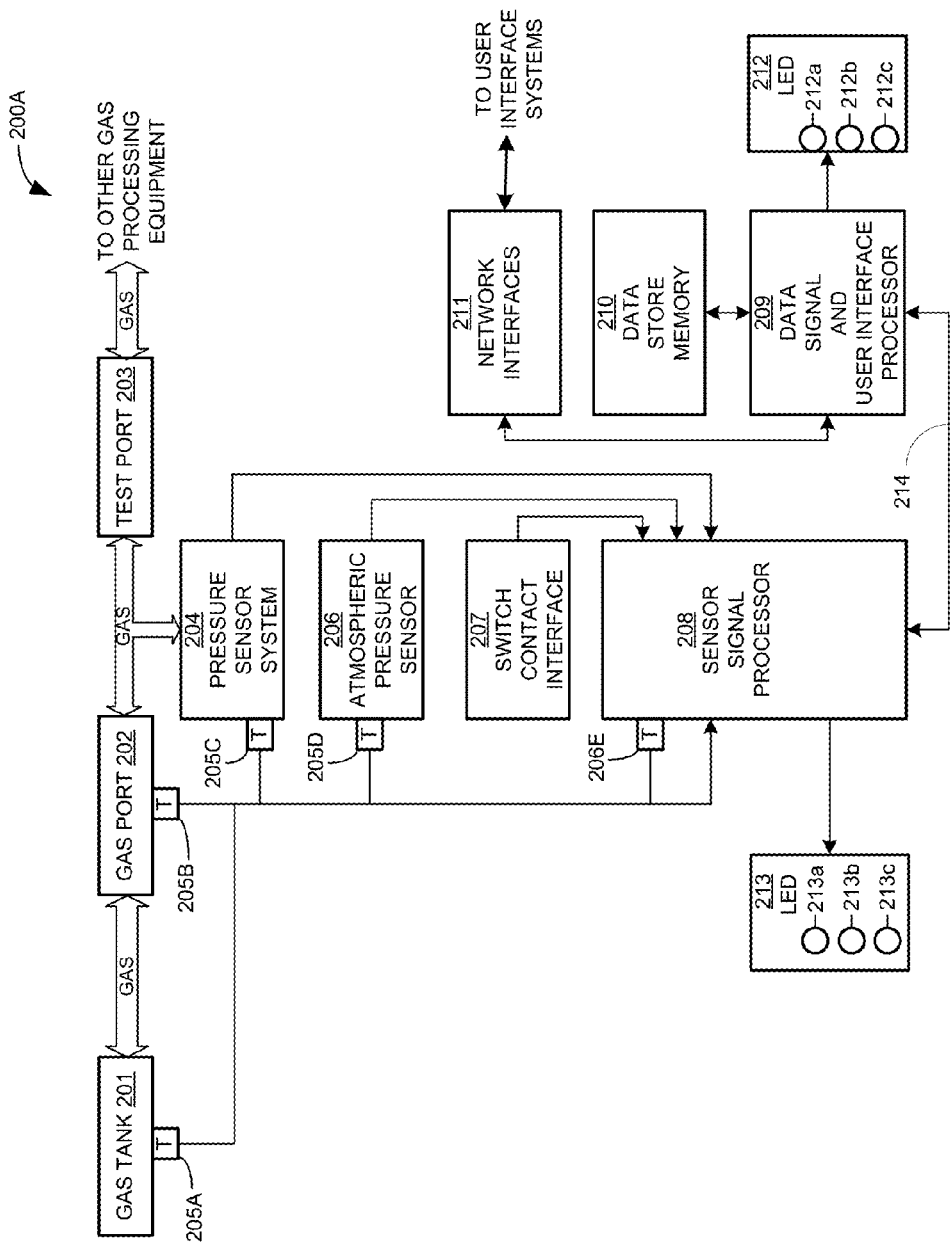
FIG. 2A is a high-level block diagram of the sensors and electronics of the apparatus.

FIG. 2A is a high level block diagram 200A of the apparatus of the present invention monitoring gas density in tank 201. One or more external temperature sensors 205A may be applied directly to the tank. Gas in tank 201 is connected to the apparatus at gas port 202 using flexible or rigid tubing material. Temperature may be measured at or near 202 using temperature sensor 205B. Gas is conveyed from the gas port to pressure sensor 204.

The pressure sensor(s) may be of any type. In one embodiment, the pressure sensor is constructed of a moveable mechanical member that moves in response to gas pressure changes. In this embodiment, the controller operates one or more position sensors providing real-time information about the displacement of the mechanical member that in turn can be processed using specific algorithms to reveal the gas pressure. The pressure indicated is differential pressure with respect to atmospheric pressure. A separate sensor measuring absolute atmospheric pressure is employed, the sum of the differential gas and atmospheric pressures indicating the absolute gas pressure. In this embodiment, the mechanical member can also be configured to actuate mechanical switches positioned to actuate at particular displacements representing particular pressure levels. In this case, the controller also operates sensors to monitor the state of the mechanical switches providing real-time information as to whether a switch is open or closed and information about the voltages present on the respective switch pole (FIGS. 2A-2C and 3). In an alternative embodiment, the pressure sensor may be of an integrated type that provides an electrical signal output proportional to pressure (FIGS. 2A, 2D-2E, and 4). An integral sensor may measure either differential pressure and be used in conjunction with an independent sensor for absolute atmospheric pressure to determine absolute gas pressure or may be an absolute pressure sensor itself measuring absolute gas pressure directly. There is an advantage to using an absolute atmospheric pressure sensor in combination with a differential gas pressure sensor in that the absolute sensor need only operate over the relatively low pressure range of 0 to 1 atmosphere. In this case there is less stress on a hermetic seal on a perfect vacuum required on the opposing side of the absolute-type pressure device. Nonetheless, any pressure measurement scheme that determines the absolute pressure of the gas for use in gas law computations is contemplated by the present invention and it is assumed when pressures are referenced herein that the appropriate pressure, differential or absolute, is implied by context.

An auxiliary gas connection is made available at one-way test port 203. This facilitates test devices or other products that require connection to the gas system to be conveniently attached. When utilized, absolute atmospheric pressure is sensed by 206. In an embodiment where a moving mechanical member responds to differential gas pressure to actuate switches, the switch contact states and voltage are monitored by the interface 207. Temperature sensors may be utilized at the locations of 204, 205, and at controller 208. These are shown as 205C, 205D, and 205E respectively. All temperature, pressure, and switch contact related signals are directed to sensor signal processor 208 wherein analog conditioning, conversion to digital format, and calibration and transformation to measurements in engineering units is performed in real-time.

Processor 208 may also utilize LEDs 213a, 213b, and 213c to signal various status information to the user in an observable way. A lesser or greater number of LED indicators is possible. Processor 208 communicates with data, signal, and user interface processor 209 via communications link 214. 208 and 209 may be physically combined in one integrated circuit, or as separate processors on one printed circuit board, or as separate processors in physically separate modules. Processor 209 stores all of the real-time measurements output by 208 into data store memory 210 and implements signal processing to render gas density and other objective measurements from the real-time information provided through processor 208. Processor 209 also support communications interfaces 211 to external user devices which may be of the type asynchronous serial, synchronous serial or USB, Ethernet, or other conventional types of network interfaces.

Processor 209 in the present invention also supports an embedded web server application that provides a convenient graphical user interface to system information via a user's standard web browser program. Processor 209 may also utilize LEDs 212a, 212b, and 212c to signal various status information to the user in an observable way. A lesser or greater number of LED indicators is possible.

Figure 2B:
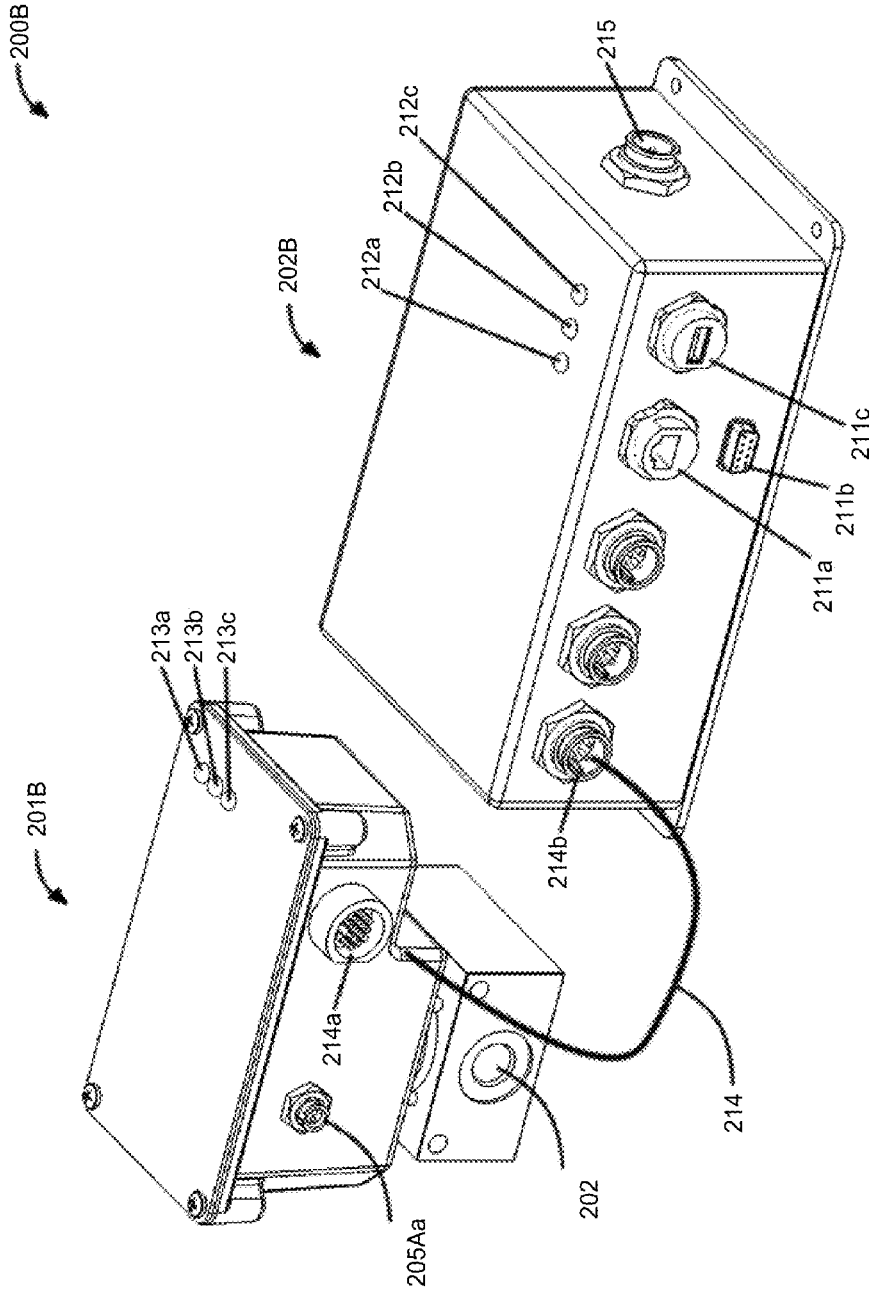
FIG. 2B is a perspective view of a first embodiment of the apparatus.

FIG. 2B is a view 200B of an embodiment where the functions are divided into two modules, sensor 201B and hub 202B. Connection 205Aa supports external temperature sensor 205A affixed to a gas tank (not shown). The connection between processor functions 208 and 209, 214, is implemented via connectors 214a and 214b. The network interfaces 211 are shown as RJ45 Ethernet connector 211a, serial connector 211b, and USB connector 211c. 215 is a power connection for external power input. Gas port 202 is shown and test port 203 is not shown but may be on the side of the block opposite gas port 202.

FIG. 2C is a view 200C of the electronics of the apparatus 200B. Switches 207A are actuated by elements 302 incorporated into a moving mechanical lever 301 shown in FIG. 3. Displacement sensors 101a are used to measure the displacement of 301, information that can then be converted to equivalent gas pressure via processing apparatus 101, 108, and 109.

FIG. 2D is a view 200D of an embodiment where the functions are incorporated into a single enclosure. Connection 205Aa supports external temperature sensor 205A affixed to a gas tank (not shown). The network interfaces 211 are shown as RJ45 Ethernet connector 211a and USB connector 211c. 215 is a power connection for external power input. Gas port 202 is shown as is test port 203.

Figure 2E:
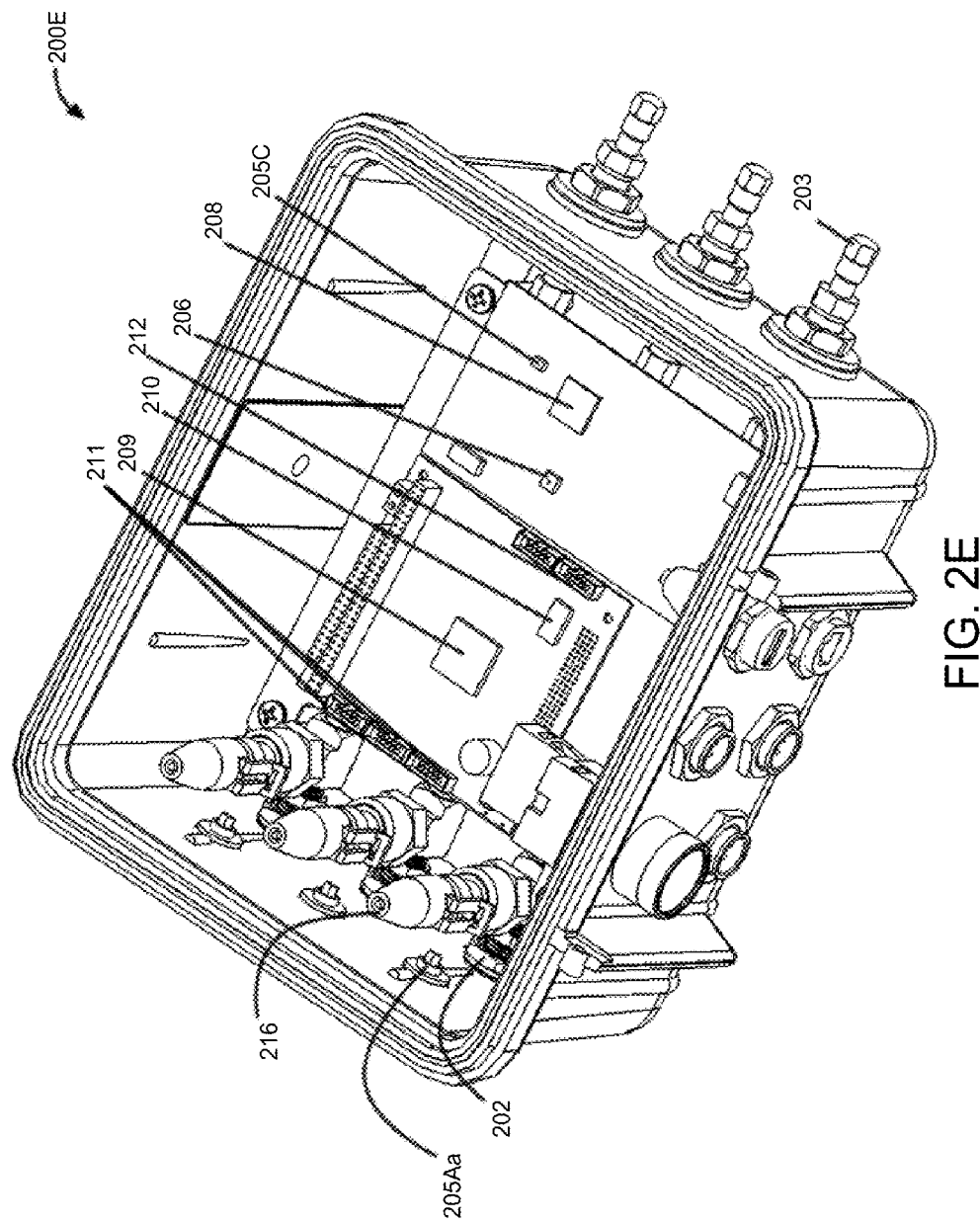
FIG. 2E is a view of the circuit board assemblies of the second embodiment.

FIG. 2E is a view 200E of the electronics of the apparatus 200D. An integral pressure sender with electrical output 216 is connected to the gas system.

Figure 3:
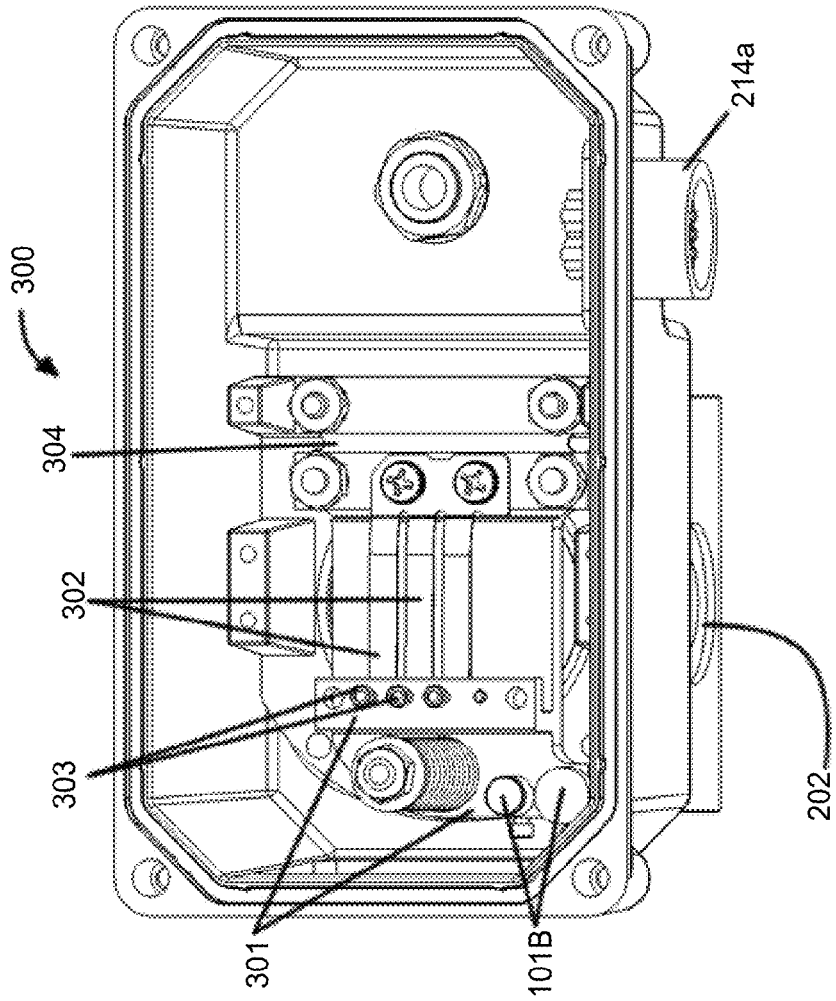
FIG. 3 is a view of the first embodiment using a moving mechanical element for pressure sensing.

FIG. 3 is a diagram 300 of the moving mechanical pressure mechanism. In this case the moving mechanical element is a lever apparatus 301, which may pivot on a hinge 304 moving an amount proportional to the pressure changes in the gas system to which the sensor is connected (not shown). Hinge 304 may be of a bi-metal construction exerting a biasing force modifying lever displacement response as a function of temperature. Displacement sensor targets 101b operate in conjunction with sensor elements 101a responding to the amount of lever displacement. Elements 302 move with lever 301 with an offset that is adjustable by adjusters 303 respectively. Elements 302 actuate switches 207A and the adjusters enable the actuation point to be set to a particular pressure threshold for each switch.

Figure 4:
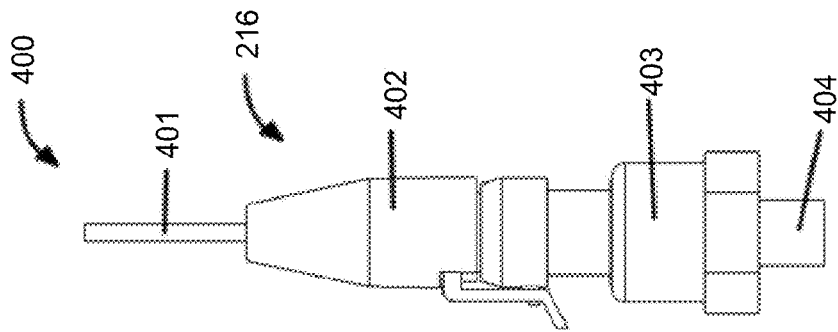
FIG. 4 is a view of the second embodiment using an integrated pressure sender with electrical output.

FIG. 4 is a diagram 400 of an integral pressure sensor with voltage output 216. Port 404 connects the sensor to the gas system (not shown). The body 403 contains the sensor apparatus that outputs an electrical signal proportional to pressure via connector 402 and conductor 401.

Returning to FIG. 1, real-time data is collected by the controller at a rate of 1 sample per time $\tau$ ($\tau=1$ second or less typically) and may include displacement sensor information (101) in the case where a moving element mechanical pressure device is employed, temperature information (103) including temperatures related to the gas tank, the pressure sensors, and ambient conditions, atmospheric pressure information (104), switch contact information (105), and system voltages (106). In the case where an integrated electrical output pressure sensor is employed, the pressure sensor output voltage is collected as real-time data (102). Whether pressure measurement is based upon displacement information or pressure sensor output voltage, a pressure detection step (107) performs compensation and calibration to convert the displacement or voltage information to accurate pressure measurements.

Still referring to FIG. 1, the signals collected are saved to the data log (121) before further processing so that all of the raw data from the system is available for future inspection and re-processing.

Signals are then digitally processed into calibrated measurements in engineering units (107) for this sample time yielding:

$T_S$ pressure sensor temperature (° C.) (109)
$T_G$ gas tank temperature (° C.) if available (109)
$P_{GAS}$ Gas pressure (psig) (108)
$P_{ATM}$ Atmospheric pressure (psia) (110)
$S_{STATE}$ density monitor switch contact states (open or closed) (111)
$V_{SO}$ density monitor switch open voltage (control system voltage, e.g. 110 VAC or 150 VDC, etc. sensed during open contact state) (111)
$V_{SC}$ density monitor switch closed voltage (should be minimal else contact degradation or over-current condition may be present) (111)
$T_{EXT}$ External temperatures (° C.) if available (109)

Figure 6A:
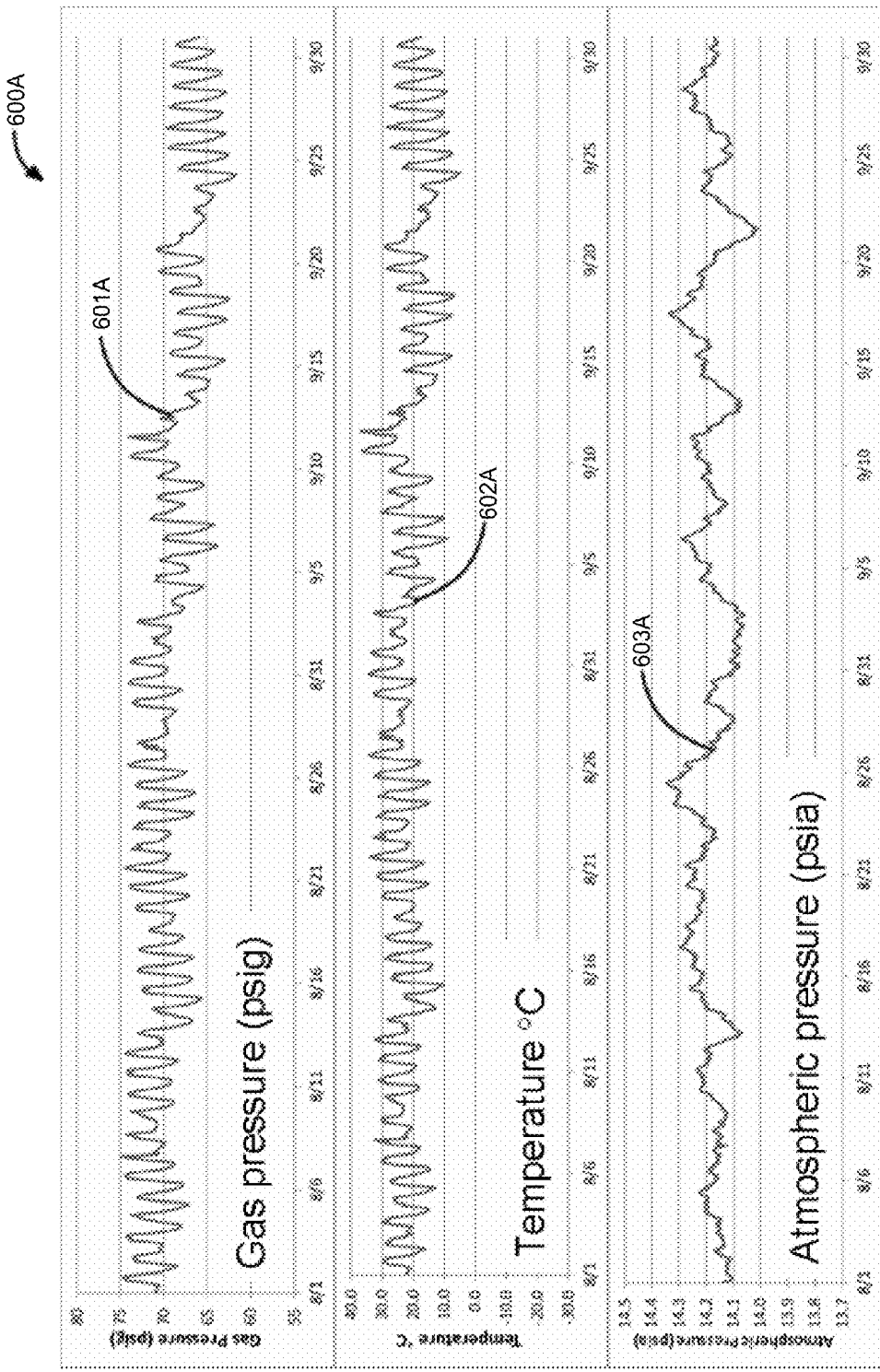
FIG. 6A is a graph showing two months of data for gas pressure, temperature, and atmospheric pressure.
Figure 6B:
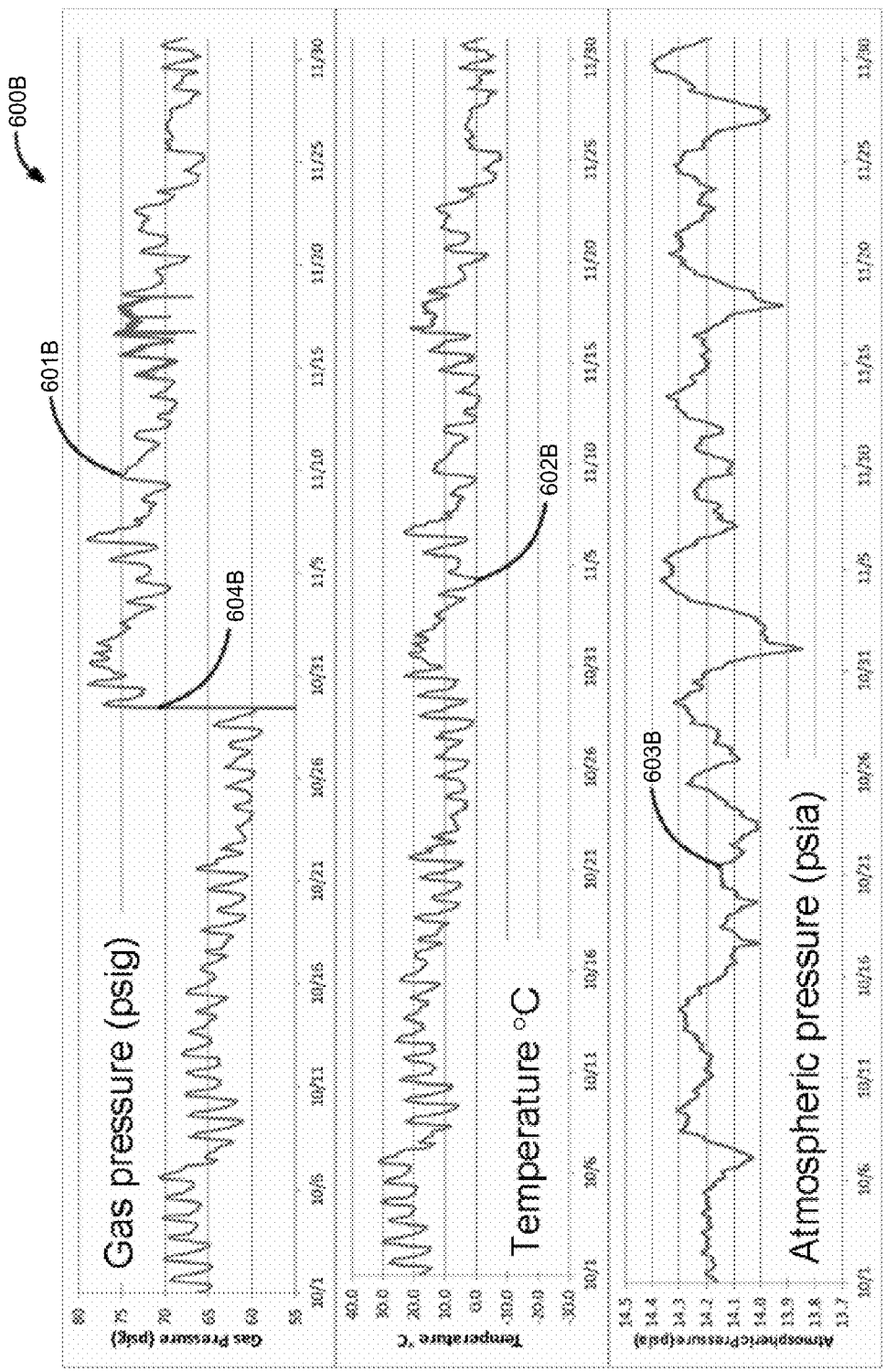
FIG. 6B is a graph showing an additional two months of data for gas pressure, temperature, and atmospheric pressure.
Figure 6C:
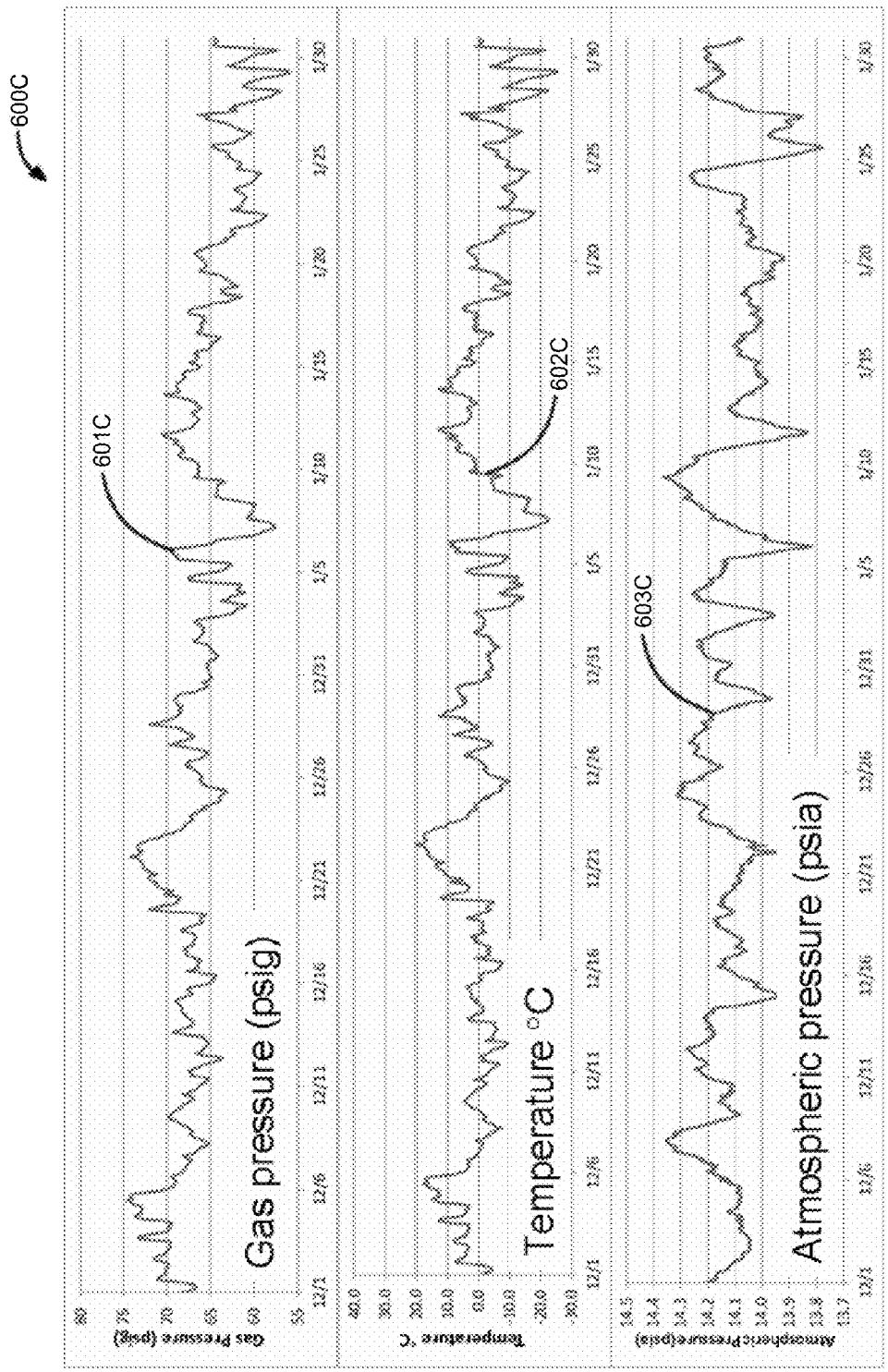
FIG. 6C is a graph showing an additional two months of data for gas pressure, temperature, and atmospheric pressure.

With it being understood that all measurements represent series in time at the real time sample rate ($1/\tau$). FIGS. 6A-6C show a representative time series 600A, 600B, and 600C for gas pressure $P_{GAS}$ (601A, 601B, 601C), gas temperature $T_G$ (602A, 602B, 602C), and atmospheric pressure $P_{ATM}$ (603A, 603B, 603C). Referring to FIG. 601B, a step change in pressure indicating a gas fill event is seen at 604B.

The second order virial equation is used to compute a real time density estimate:

$$\text{Virial equation: } P = R \cdot T \cdot \left( \frac{n}{V} + B(T) \cdot \frac{n^2}{V^2} \right) \quad (3)$$

The coefficient function B(T) is the second order virial coefficient and is estimated using a function of the gas type and the absolute temperature of the gas. An example function is:

$$\text{Second order virial coefficient } B = a - b \cdot e^{\frac{c}{T}} \quad (3a)$$

where a, b, and c are constants specific to the gas type and T is the absolute temperature of the gas.

Once the coefficient B is calculated, it may be used in the following formula to calculate gas density:

$$\text{Gas density: density} = \frac{\left( \sqrt{R^2 \cdot T^2 + 4 \cdot B \cdot P \cdot R \cdot T} - R \cdot T \right)}{2 \cdot B \cdot R \cdot T} \quad (3b)$$

where R is the universal gas constant, P is absolute gas pressure, T is absolute gas temperature, and density is in units of mass per unit volume.

When a dedicated temperature sensor is not available to measure the gas tank temperature, the pressure sensor temperature $T_S$ is used in place of $T_G$. Where $d_{RT}(t)=n/V$ is the gas density sought, $P=P_{GAS}+P_{ATM}$ is absolute pressure, $T=T_G+273.15$ absolute temperature, R is the gas constant, and B(T) is the temperature dependent second order virial coefficient for the particular gas, often $SF_6$.

The density estimate can be further used to compute a temperature corrected pressure, $P_{20}$ for example, the corresponding gauge pressure at the reference temperature of 20° C. (or other reference temperature).

At any instant in time, an error in $d_{RT}(t)$ relative to the actual gas density $d(t)$ will arise from several factors including errors in the measurements of $T_S$, $T_G$, $P_{GAS}$, and $P_{ATM}$, and, perhaps most significantly, from the deviation of $T_G$ from the actual, effective gas temperature $T_{GAS}$. For a real world system, this latter deviation is characterized by $-5.2°$ C.$<=T_S-T_{GAS}<=+7.9°$ C. leading to density estimate errors of approximately $-1.6<=d_{RT}-d<=0.9$ kg/m$^3$. With densities in the vicinity of 32 to 35 kg/m$^3$ this corresponds to an error in $d_{RT}(t)$ of up to 8% at times of greatest temperature skew. Further processing is needed to reduce this error and will be discussed below.

Figure 5:
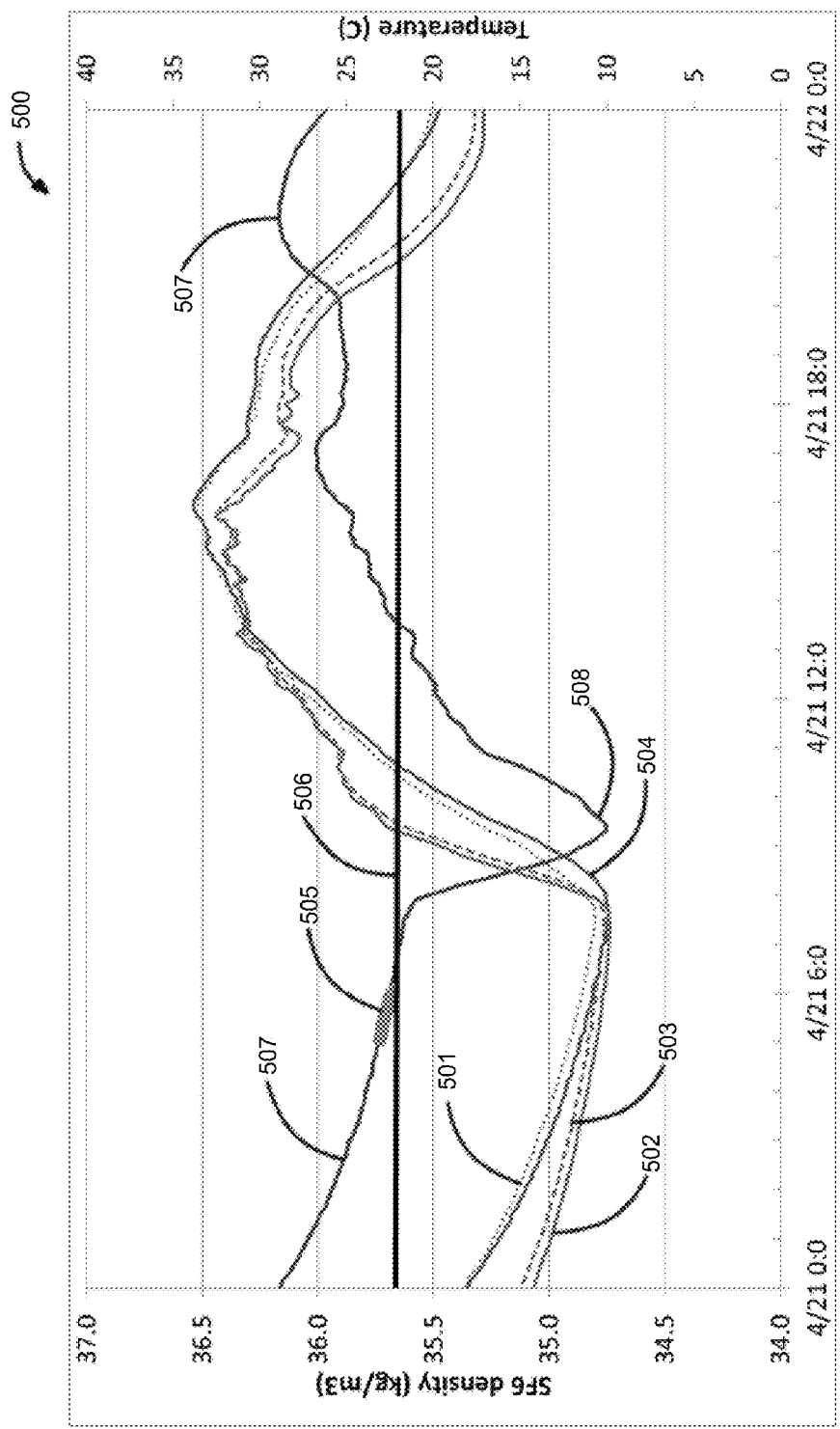
FIG. 5 is a graph showing temperature disparities over a day and the errors that depend upon the disparities.

FIG. 5 is a graph of real-time data 500 just described over a 24-hour period. Four temperature sensor curves are shown. Curve 501 corresponds to $T_G$. Curve 502 corresponds to $T_S$. Curve 503 is a second, independent measurement of $T_S$. Curve 504 is an inferred estimate of $T_{GAS}$, the effective gas temperature. The two curves for $T_S$ 502 and 503 track one another well. The $T_G$ curve 501 and the $T_{GAS}$ curve 504 also track well. Curve 506 is the long-term density estimate $d_{LT}(t)$ that depends upon the representative diurnal density samples 505 in a way that will be discussed under diurnal processing techniques below. The curve identified with 507 and 508 is the real-time density estimate $d_{RT}(t)$ described in the preceding paragraph. The regions of $d_{RT}(t)$ marked 507 of the real-time density curve are greater in magnitude that the long-term density estimate curve 506. The region of $d_{RT}(t)$ marked 508 is less than the long-term density estimate. $d_{RT}(t)$ is calculated based upon the sensor temperature measurements $T_S$ 502, 503. Regions 507 occur when $T_{GAS}$ temperatures 501, 504 exceed temperature $T_S$ 502, 503. This typically occurs when the ambient temperature is falling and the gas temperature lags the sensor cooling process. Region 508 occurs when $T_{GAS}$ 501, 504 is less than $T_S$ 502, 503. This typically occurs when the ambient temperature is rising and the gas temperature lags the sensor heating process.

Figure 7A:
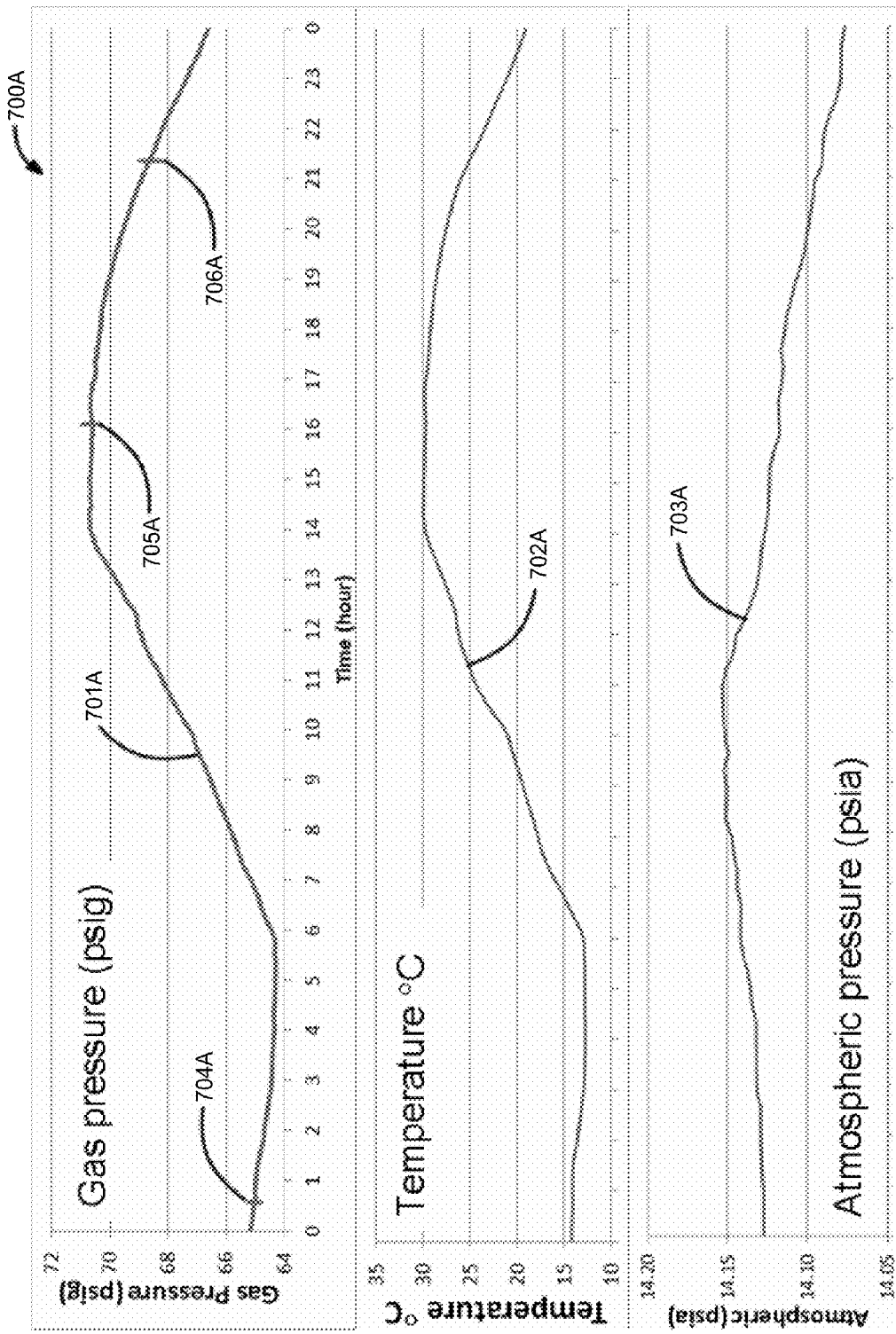
FIG. 7A is a graph showing 24-hour data for gas pressure, temperature, and atmospheric pressure.
Figure 7B:
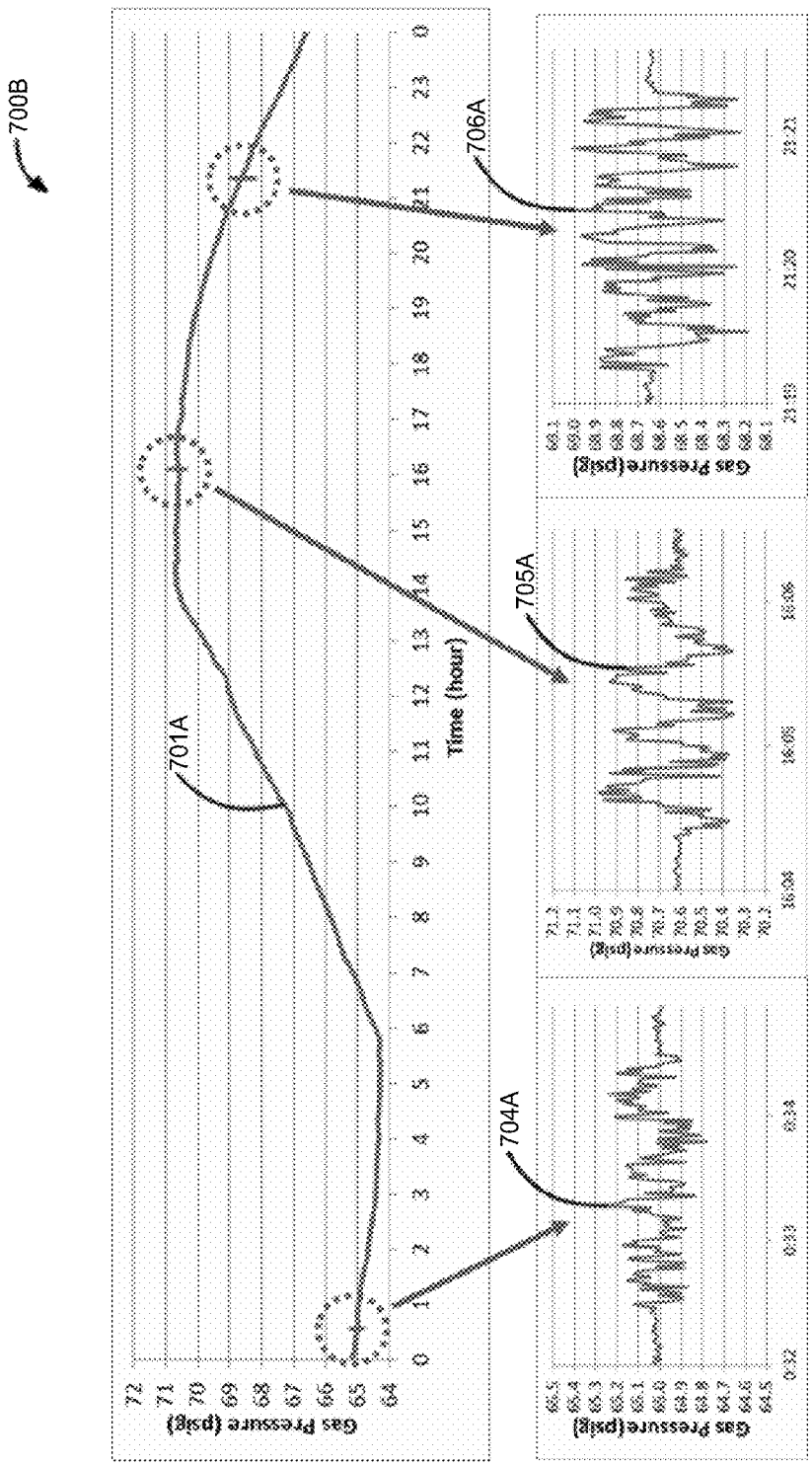
FIG. 7B is a graph showing 2-minute segments of 24-hour data for gas pressure.
Figure 7C:
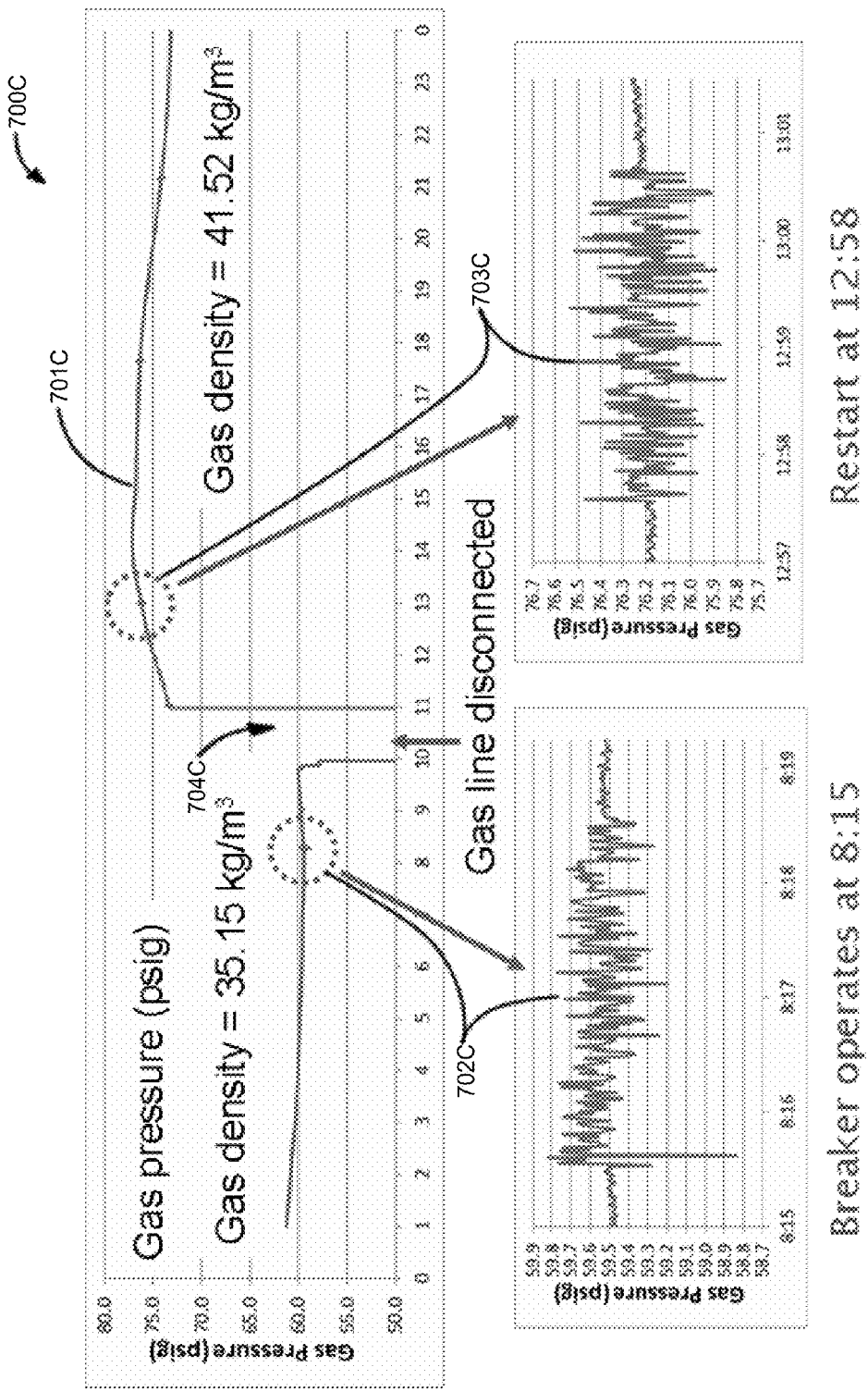
FIG. 7C is a graph showing 5-minute segments of 24-hour data for gas pressure.

The $P_{GAS}(t)$ real time pressure series 701A and 701C shown in the graphs 700A-700C of FIGS. 7A-7C is also used to detect high speed events such as breaker operation (702C, 703C), compressor operation (704A, 705A, and 706A), and other ambient vibration events such as technician activity, thunder, wind, etc. A gas fill event is indicated in the region 704C.

Figure 8A:
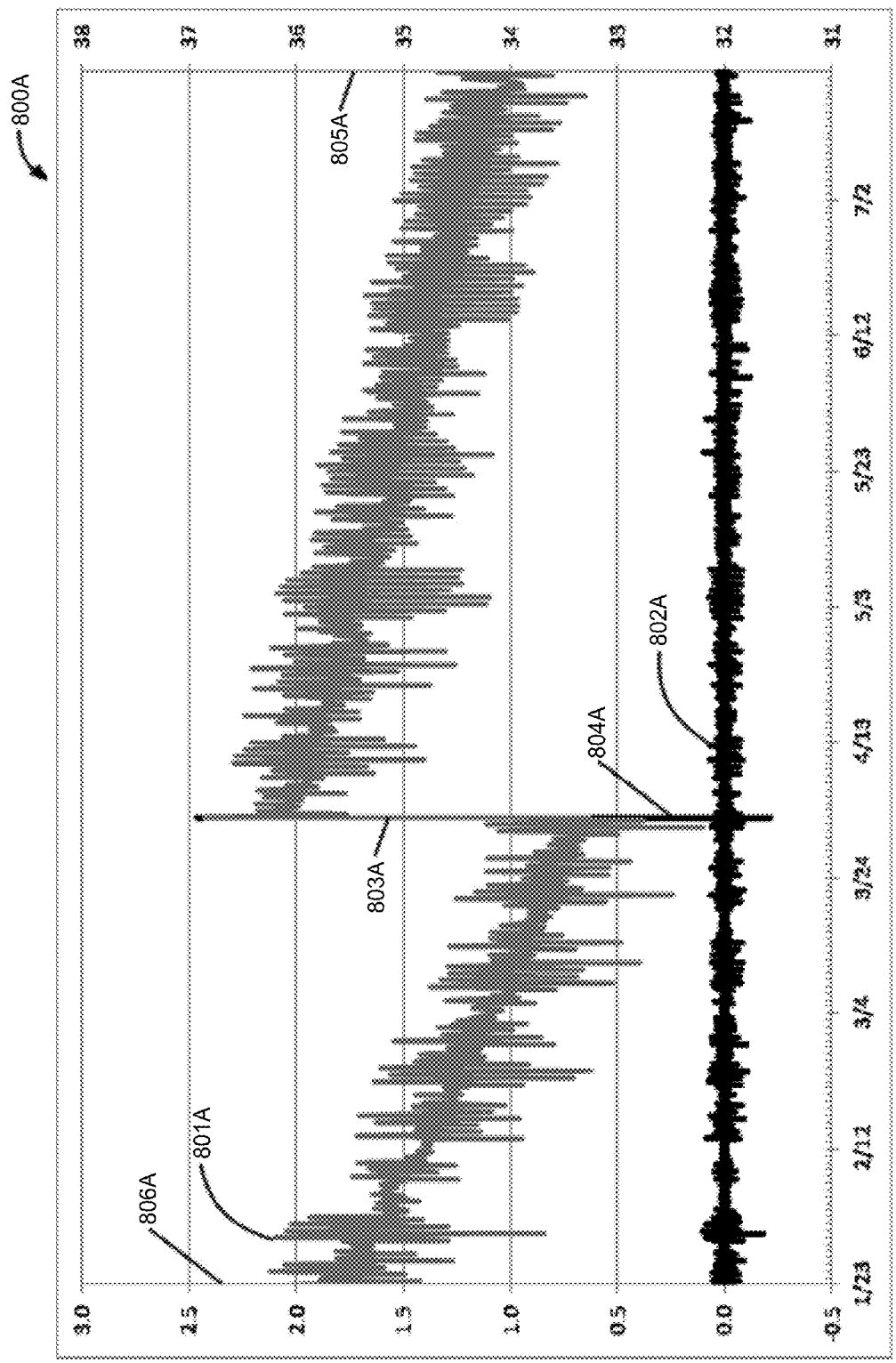
FIG. 8A is a graph showing first difference of short term density $dd_{ST}$.

FIG. 8A is a graph 800A having a density axis 805A scaled in units of kg/m$^3$ and a density difference axis 806A also with units of kg/m$^3$. Short term ($\tau=1$ minute to 5 minutes typically) processing uses the real-time data. Referring again to FIG. 1, the real time series $d_{RT}(t)$ is processed through a short-term low pass filter mechanism (115) to yield a time series $d_{ST}(t)$ (801A) shown in FIG. 8A-8B. This tends to cancel short-term noise attributable to measurement variations producing a reliable data stream that can be used to detect significant, short-term steps in gas density such as those that occur during a gas fill or result from a fast gas loss from either maintenance activity or catastrophic leak events. 803A is the density variation associated with a gas fill event.

Figure 8B:
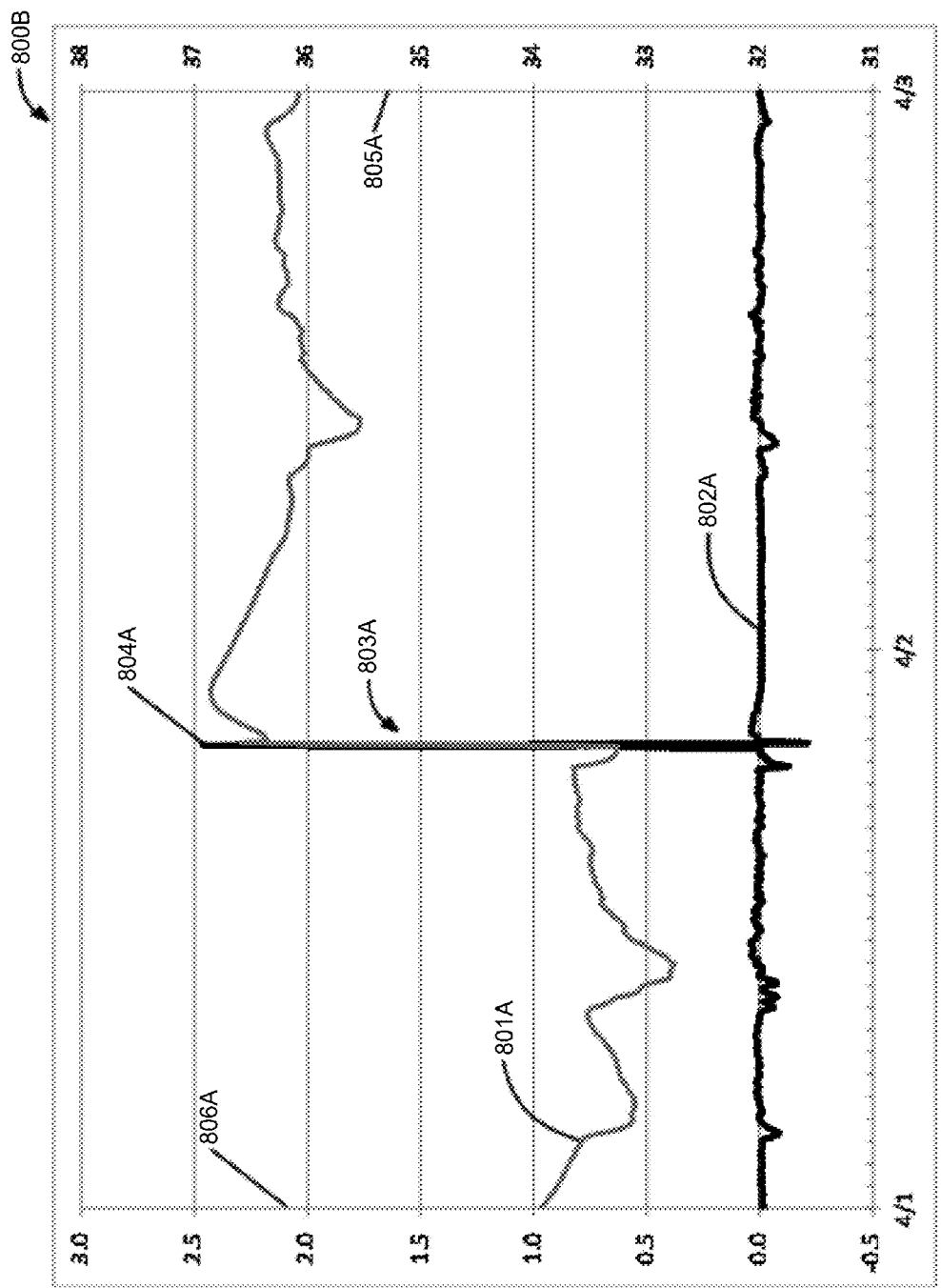
FIG. 8B is a graph showing the data of FIG. 8A at higher resolution (shorter timeframe).

A select difference of the short term density series, $dd_{ST}(t)=d_{ST}(t)-d_{ST}(t-N*\tau)$, implemented in processing block 118, is used to detect density steps. FIG. 8A shows $dd_{ST}(j)$ (802A) for the test period of a typical breaker where $N=300$ (and $\tau=1$ second) implying a 5-minute difference. FIG. 8B zooms to the time of a gas fill event. When $dd_{ST}(t)$ exceeds a threshold, a density step is inferred and density step processing commences (see below). The density step depicted at 803A is clearly revealed by the $dd_{ST}(t)$ difference function at 804A.

This information, $d_{ST}(t)$ and $dd_{ST}(t)$, will be used to adapt the short-term, diurnal, and long-term density estimates during step change events and to provide for a smooth transition of time to alarm and lockout estimates even in the presence of step change events.

Regarding the detection of significant short-term density changes, two additional mechanisms are employed, also implemented in processing block 118. First, the value of $d_{ST}(t)$ is compared to the current long-term density estimate $d_{LT}(t)$ (see below). When ABS($d_{ST}(t)-d_{LT}(t)$) exceeds a particular threshold, a density step is inferred and density step processing is invoked. Second, when the day-to-day difference in long-term density estimate compared to the representative diurnal density estimate assessed following the flattest temperature region, ABS($d_{DR}(t_{BEST})-d_{LT}(t_{BEST})$), exceeds another particular threshold, a density step is inferred and processed. This is explained in detail below.

During periods of relatively slow changes in gas density (slow leaking for example), diurnal processing, implemented in processing block 116, is used to establish a daily density time series based upon selecting a period for each day where the least variation in gas temperature $T_G$ is found and therefore perhaps the time where the closest alignment of $T_G$ or $T_S$ with the effective gas temperature $T_{GAS}$ occurs. The processing uses several parameters, each of which is programmable, as follows:

$H_{BS}$ the hour of the day to begin seeking the flattest temperature region, for example 4 am $H_{ES}$ the hour to stop seeking the flattest temperature region, for example 8 am $\Delta t_{RSMIN}$ the minimum region in time to select, typically 1 hour. The selected region can be longer if the stable temperature persists.

$\Delta t_{SS}$ the sample size in time to process selected at the end of the flattest region found, i.e. when the temperature has been most stable for the longest time, for example 5 minutes.

Figure 9:
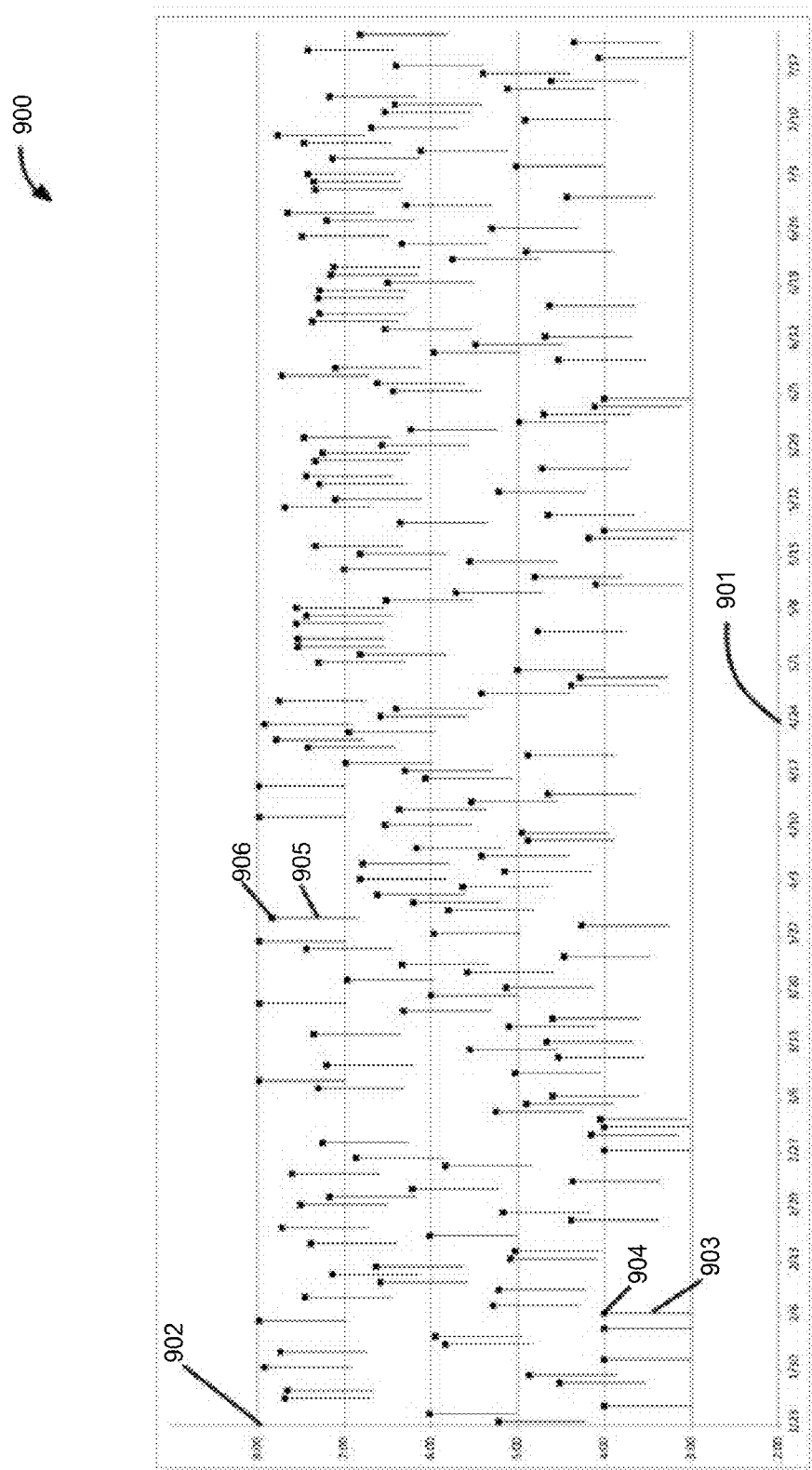
FIG. 9 is a graph showing the daily selection of least temperature variation of the gas system.

Processing proceeds examining $T_G(t)$ over a sliding window of $\Delta t_{RSMIN}$ size positioned initially at $t=H_{BS}$, sliding along a single real time sample (e.g. one second) at a time until $t=H_{ES}$. As each window is considered, the RMS value of $T_G(t)$ over the window is calculated and the location of the window having the minimum RMS value is noted. When a new minimum RMS value is encountered, the window size is extended from that location providing that the RMS value remains the same or less for each sample by which the window is extended. When the window early edge arrives at $H_{ES}$, a window having the minimum RMS value of $T_G(t)$ of size $\Delta t_{RSMIN}$ or larger is known. A sample of size $\Delta t_{SS}$ is then selected from the latest portion of the minimum RMS window at time $t_{BEST}$, for processing with the thought that this represents the best time to estimate gas density based upon $T_G$ for the day in question (the time when $T_G$ most closely represents $T_{GAS}$ for that day). FIG. 9 is a graph 900 with axis 901 in increments of days and axis 902 spanning 2 A.M. to 9 A.M. timeframes each morning. The 1-hour time windows (for example 903 and 905) are shown selected on a daily basis for having the lowest temperature variation in the morning timeframe for a typical high-voltage breaker over a period of approximately six months. The sample regions $\Delta t_{SS}$ at the end of the window representing $t_{BEST}$ for the day (904 and 906) are also shown.

Figure 10:
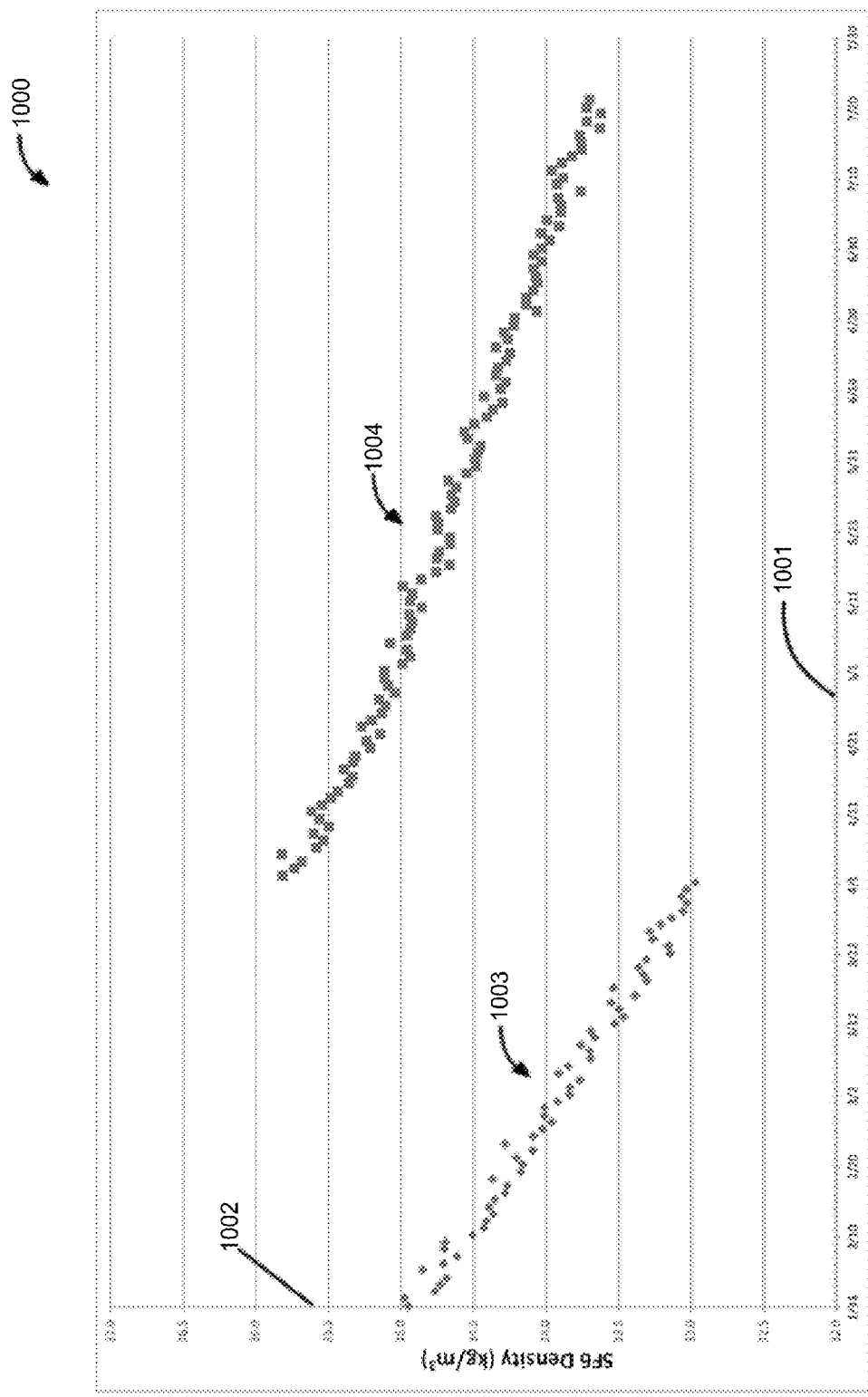
FIG. 10 is a graph showing the representative diurnal density estimate series.

Since $\Delta t_{SS}$ represents a small amount of time during which only infinitesimal changes in density are expected, the values of $P_{GAS}$, $P_{ATM}$, and $T_G$ are simply averaged over the interval and the respective average values then used to calculate a representative gas density for the day $d_{RD}$ at the particular time of the sample for that day $t_{BEST}$. This process creates a new sequence of density, sample-time data pairs $<d_{RD}(day), t_{BEST}(day)>$ called the representative diurnal density estimate series which will be used subsequently in long-term processing. FIG. 10 is a graph 1000 showing the $d_{RD}(day)$, $t_{BEST}(day)$ (1003 and 1004) series points for a typical high-voltage breaker. Axis 1001 is in units of date and time and axis 1002 is in units of gas density, $kg/m^3$.

Long term processing operates on data covering one to many days and is implemented in processing block 117. The goal of long-term processing is to effectively compensate for errors in real-time density estimates $d_{RT}(t)$ relative to the actual gas density $d(t)$ that occur as a result of the factors mentioned above including errors in the measurements of $T_G$, $P_{GAS}$, and $P_{ATM}$, and the large deviation of $T_G$ from the actual, effective gas temperature $T_{GAS}$ witnessed in practice. The mechanism utilizes the representative diurnal density series, conceptual model(s) of the gas leak process, and curve fitting algorithms.

Regression analysis may be used in long-term processing. Whenever representative density points $d_{RD}(day)$ are available for three (3) or more days running, a regression analysis may be performed. A regression model and the number of samples over which to compute the regression function are chosen. For example, exponential regression analysis can be used as follows:

Long-term density estimate: $d_{LT}(t)=b \cdot e^{(a \cdot t)}$ based upon best fit exponential function (4)

Coefficients a and b are calculated to minimize the squared error:

$$\text{mean squared error: } ERROR^2 = \sum_N (d_{RD}(t_i) - d_{LT}(t_i))^2 \quad (5)$$

In an alternative embodiment, any appropriate function that utilizes any of the real-time, short-term, diurnal, or long-term information may be used to estimate the gas density. In general terms:

Generalized Long-Term Density Estimate:

$$d_{LT(t)} = f(T_S, T_G, P_{GAS}, P_{ATM}, S_{STATE}, V_{SO}, V_{SC}, T_{EXT}, d_{RD}, t_{BEST}, t) \quad (6)$$

where it is understood that each independent variable with the exception oft time represents a time series of samples acquired or calculated as described in the preceding paragraphs. Curve-fitting models including linear, polynomial, and non-linear decline models such as exponential or hyperbolic decline are all contemplated in the present invention.

The exponential regression by way of example is a useful model for real world leaks where the rate tends to decrease with decreasing pressure (the scenario where gas escapes from a fixed volume at constant temperature through a leak port of fixed resistance to gas flow). In the real world, however, leaks tend to evolve over time as other factors including temperature effect on gas viscosity come into play. Gas viscosity impacts leak rates (higher temperature implies higher gas viscosity which in turn implies lower leak rates). For this reason, the present invention can limit the number of $d_{RD}(day)$, $T_{BEST}(day)$ points included in the long term density estimation to some number of most recent points on the assumption that older points may no longer represent current leak trends. In one embodiment, the most recent 30 days samples are utilized. This is an example of a reasonable compromise between rejecting errors due to temperature disparities and larger samples spanning longer periods during which leak mechanisms may have changed due to a number of factors.

Figure 11:
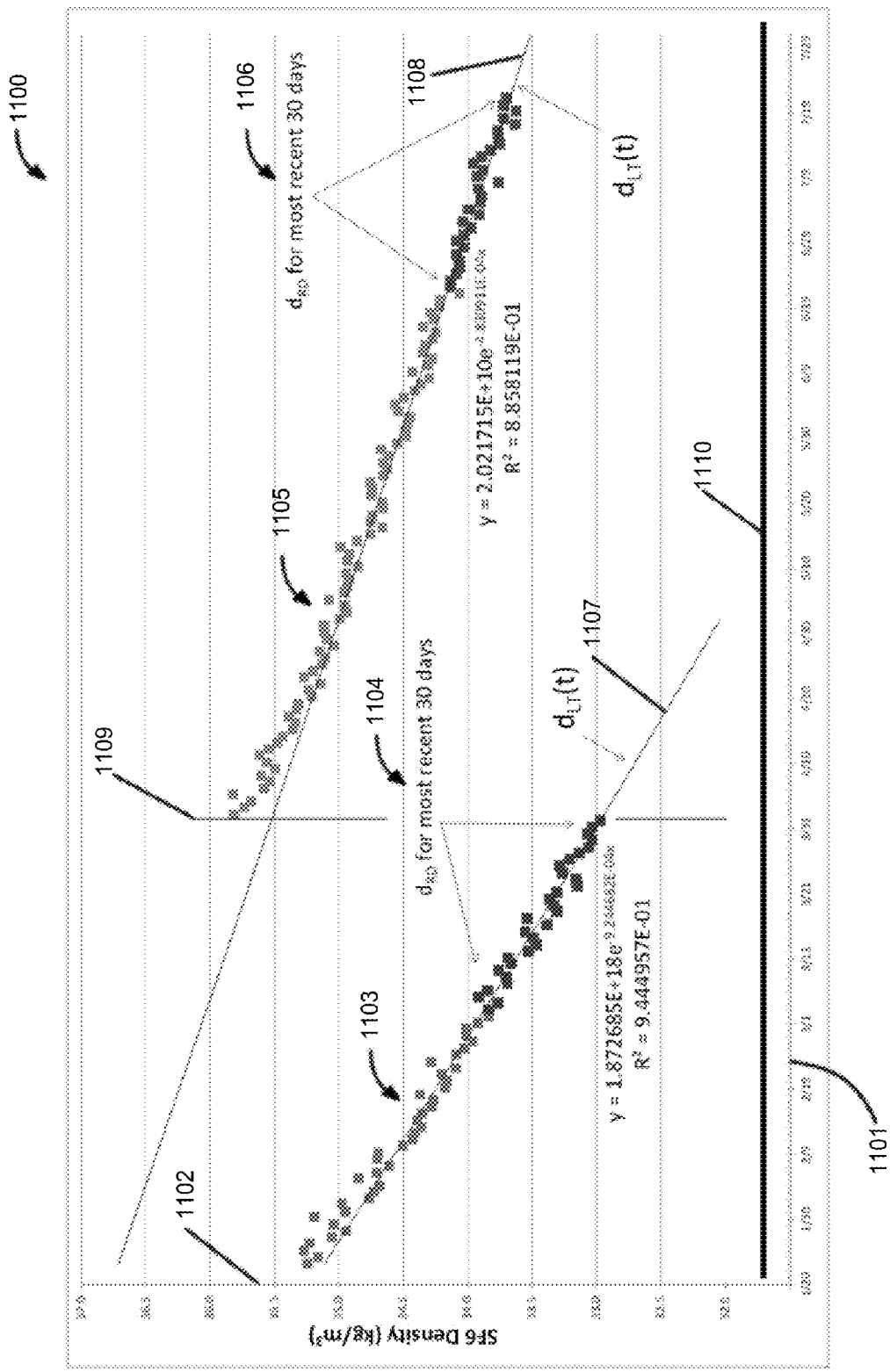
FIG. 11 is a graph showing a regression on the representative diurnal density estimate series.

FIG. 11 is a graph 1100 with axis 1101 in units of date and time and axis 1102 in units of gas density, $kg/m^3$, showing the representative diurnal density series for two eras, 1103 plus 1104 and 1105 plus 1106. The latest 30 days of each era, 1104 and 1106 respectively, have been used in long-term processing 117 to compute long-term density $d_{LT}(t)$ estimation functions 1107 and 1108 respectively. In this example, the exponential regression mentioned above was used. At any instant, the long term density estimate $d_{LT}(t)$ is defined by the value of the applicable best-fit function evaluated at time t.

As described above, each day, a region of least temperature variation is identified and used to calculate a representative diurnal density estimate thought to reflect the smallest error, for the day, attributable to the difference between sensor temperature and effective gas temperature. As each point is added to the representative diurnal density estimate series, an exponential regression or other leak model function is applied over points including it and a number of preceding points determined by a lookback parameter setting, typically 30 points equivalent to 30 days inclusive. The regression analysis yields two coefficients that determine the best fit (least squared error) exponential function over the data. This process gives rise to two new series, $a_n$ and $b_n$, where n is an index representing the current day and a and b are the coefficients of the most recent regression analysis run at the time of day just after the representative diurnal density estimate for day n becomes available.

Most recent long term density estimator: $d_{LT}(t) = b_n \cdot e^{(a_n \cdot t)}$ for example, over the last 30 days (7)

The next step is to adapt to variations in a leak rate and to predict the time when the gas density will reach a particular threshold level. At any given time, the most recent long term density estimator is used to estimate the current density simply by evaluating the exponential equation with coefficients $a_n$ and $b_n$ for the current time t. The current density estimate so derived is reported to the user interface (see below) as "Density Estimate" and the coefficient of determination, so-called $R^2$ value, is reported as the "Density Estimate Confidence". $R^2$ is both a function of the number of points in the analysis (fewer points typically yields lower confidence) and the degree to which the exponential estimator function matches the actual representative diurnal density points.

Conversely, for a particular density of interest, for example the density representing a lockout or alarm threshold, one can solve for the time when the exponential estimator will intercept that density. For example:

$$\text{Time when density is predicted to reach lockout level: } t_{lockout} = \frac{\ln\left(\frac{d_{lockout}}{a_n}\right)}{b_n} \quad (8)$$

Figure 12A:
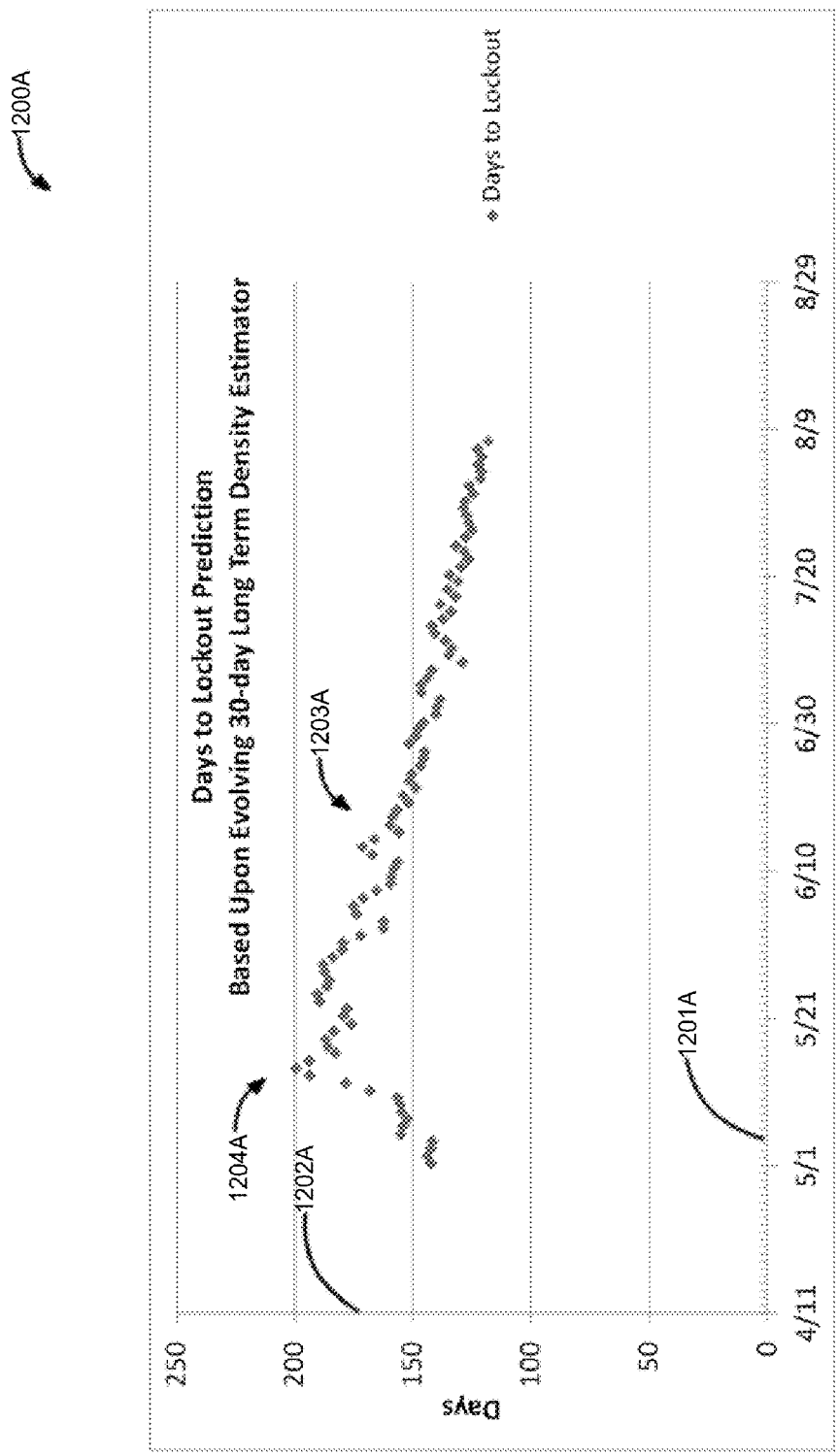
FIG. 12A is a graph showing the estimated time to lockout density level as it evolves day to day.

Using this equation along with the current long term density estimator it is possible to track the evolution of the time-to-lockout solution, lockout representing a particularly significant, low density level where safe operation of the breaker is no longer possible. For example, a typical high-voltage breaker lockout level is 31.7 kg/m³ $SF_6$ gas denoted by threshold line 1110 in FIG. 11. The example breaker was at a level of approximately 33 kg/m³ on 4/2 and was filled to a level of approximately 35.8 kg/m³ at time 1109 in FIG. 11. As of 5/1, 30 days of representative daily estimates are available to generate the evolving regression $a_n$ and $b_n$ coefficient series. FIG. 12A shows how each day's estimator predicts time to lockout in days 1203A as the long-term density estimator evolves day by day. An underlying leak rate can be seen to be slowing as the early points in 1200A show an increasing time to lockout as time progresses. This pattern changes in the vicinity of points 1204A and the leak rate begins holding steady or decreasing as the time to lockout now changes at the rate of approximately one day per day.

Figure 12B:
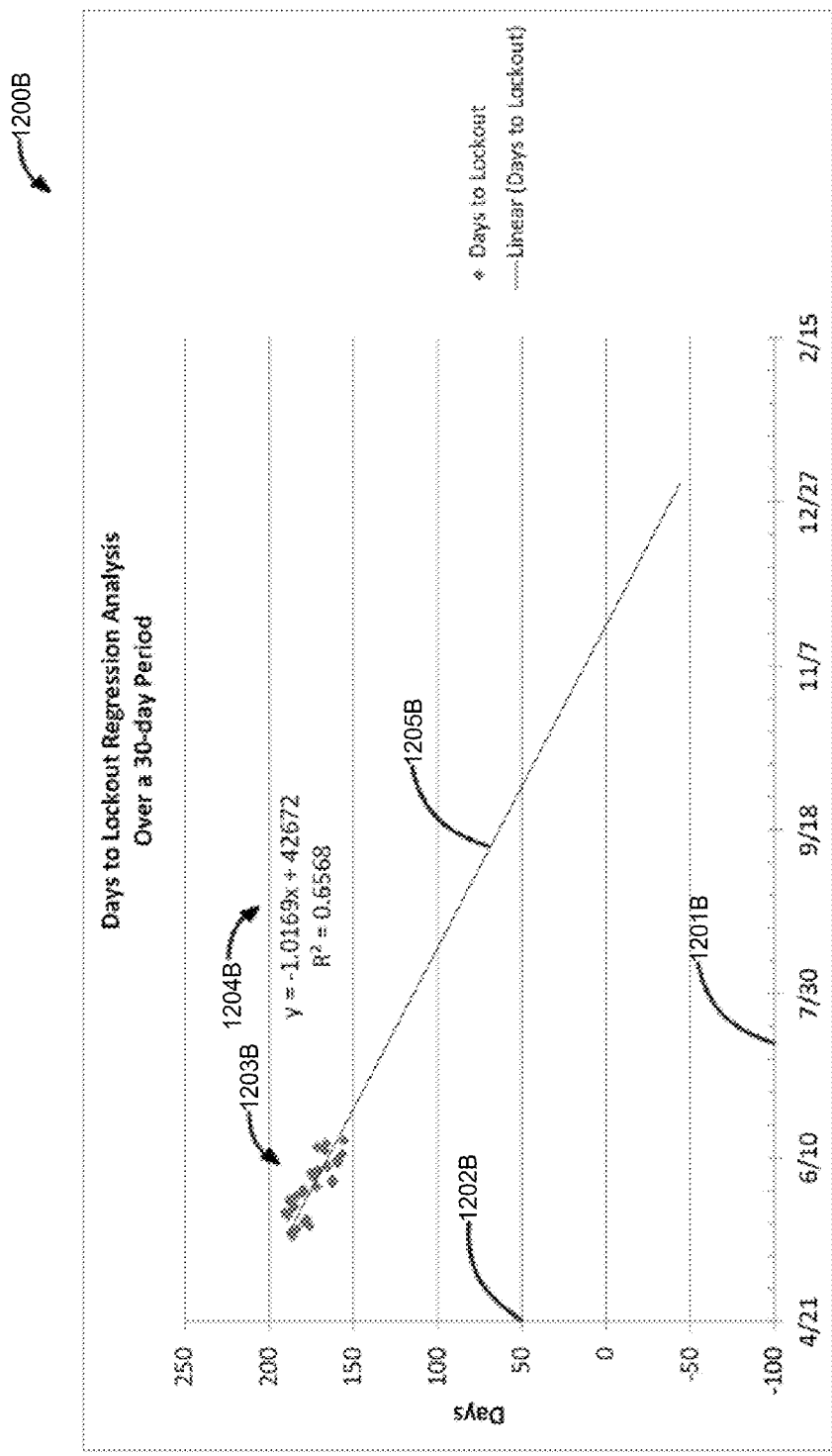
FIG. 12B is a graph showing the estimated time to lockout based upon May data points.

Changes in time to threshold events can be modeled yet again by the application of regression analysis and low pass filtering. FIG. 12B depicts a graph 1200B of linear regression analysis 1205B with statistics 1204B computed over 30 days of time-to-threshold estimates 1203B soon after the density settled in May following the fill at time 1109. The indicated leak rate is evolving such that the time to threshold progresses slightly faster than one day per day, approximately 1.02 days per day.

Figure 12C:
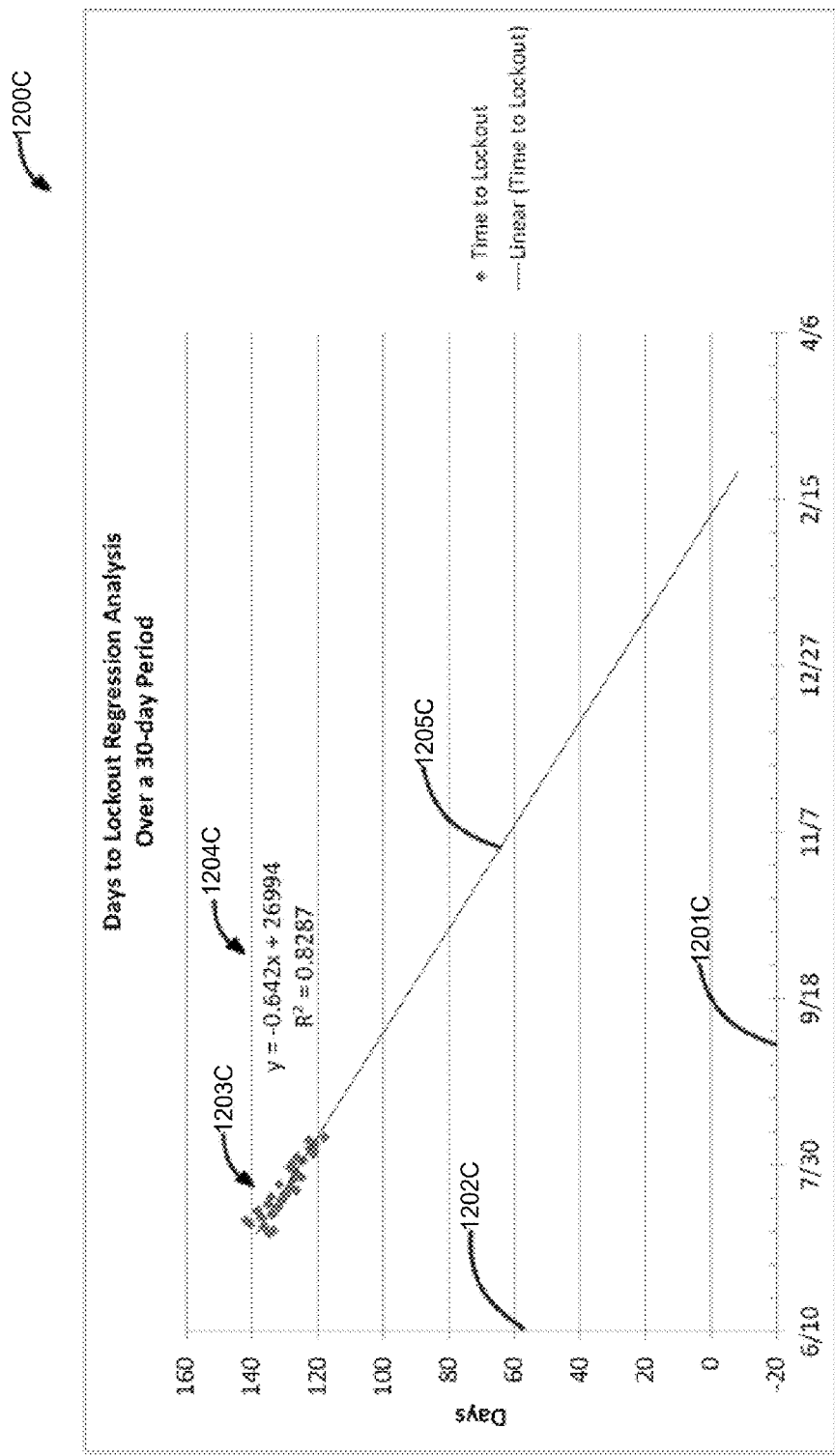
FIG. 12C is a graph showing the estimated time to lockout based upon August data points.

FIG. 12C depicts a graph 1200C showing how these time to threshold projections evolve several months later as indicated by the linear regression analysis 1205C with statistics 1204C computed over 30 days of time-to-threshold estimates 1203C beginning late July. The indicated leak rate has evolved such that the time to threshold progresses slightly slower than one day per day, approximately 0.65 days per day.

The linear regression is well behaved in terms of converging to 0 days to threshold event as the time of the threshold event approaches. In other words, it is increasingly accurate as the time to event diminishes. As mentioned above, additional filtering of the low pass variety is helpful.

Detecting relatively abrupt changes in density poses a second challenge that the present invention addresses. A select difference of the short term density series $dd_{ST}(t)$ introduced in FIGS. 8A-8B is utilized along with the short term density estimate $d_{ST}(t)$ as follows to detect and abrupt change and trigger transition processing:

$$ABS(dd_{ST}(t))=ABS(d_{ST}(t)-d_{ST}(t-N*\tau))>\text{THRESHOLD}_1 \qquad (9)$$

Another mode change detection process used to trigger transition processing utilizes the value of $d_{ST}(t)$ comparing it to the current long-term density estimate $d_{ST}(t)$:

$$ABS(d_{ST}(t)-d_{ST}(t))>\text{THRESHOLD}_2 \qquad (10)$$

A third mode detection process utilizes the day-to-day difference in long-term density estimate compared to the representative diurnal density estimate assessed following the flattest temperature region:

$$ABS(d_{DR}(t_{BEST})-d_{LT}(t_{BEST}))>\text{THRESHOLD}_3 \qquad (11)$$

Note that each process utilizes a potentially unique, respective value for THRESHOLD. When one of the above density change triggers occurs, blending models described below are invoked to provide a sensible transition in predictive modeling. This is contrasted to the prevalent situation when slow density changes occur day to day such that none of the above triggers occurs in which case the diurnal and long term processing as described above work to track such slow transitions.

The blending models invoked when abrupt changes in density are detected are an important aspect of the present invention. For the sake of example, assume that an abrupt change will be detected as a result of a fill event such as the event shown just before 4/2 at time 1109 of FIG. 11 and seen in FIG. 8B. The change would be easily detected by data 801A compared to 804A via equation (9) assuming $\text{THRESHOLD}_1<2$ kg/m$_3$. The long-term leak rate $d_{LT}$(time-of-1109) is defined by regression line 1107 and is assumed by the blending process to persist once the fill has completed at time $t_S$. The new density level, in lieu of any long-term density estimates being available after the fill completes, is assumed to be the post-fill density level estimated using either the real-time estimate $d_{RT}$ (time-after-fill) or the short-term estimate $d_{ST}$ (time-after-fill). The density level going forward then will be estimated with greater confidence as representative diurnal density estimates become available and a current regression line such as 1108 becomes available. The process of making the transition in density estimates from the time of the step to the well established long-term estimates later on is represented by a system of equations as follows. The subscript r denotes real-time, short-term, or current regression coefficients, i.e. coefficients measured after the step, and subscript w implies working values during the period of transition or blending following the density step at time $t_S$:

$$\text{Working density constraint: } b_w \cdot e^{a_w \cdot t_s} = b_r \cdot e^{a_r \cdot t_s} \qquad (12)$$

The working density from the time of the step forward should match the best current estimate. Until a representative diurnal estimate is available, this will be the real-time or short-term density as mentioned above. As representative diurnal samples accrue, an improved density estimate will be available by considering the evolving long-term density estimate $d_{ST}(t)$ generated by the evolving regression analyses 1108. The working density is used to bridge this transition and is modeled as a blend of the current real-time rate and the rate in evidence just before the density step $a_{PRESTEP}$ as follows:

$$\text{Transition working rate constraint: } a_w = \alpha \cdot a_r + (1-\alpha) \cdot a_{PRESTEP} \qquad (13)$$

where $a_w$ is the working rate of density change in transition, $a_r$ is the real-time or short-term density rate measured beginning after the step, and $a_{PRESTEP}$ is the rate operating in the long-term density estimate according to regression line 1107 just before the step.

Equation (13) portrays the working density change rate as a smooth transition between the prior pre-step rate and the rate determined by the evolving regression analyses using the parameter α, a fraction, increasing toward unity over a programmed number of days N as follows:

$$\text{Transition rate weighting parameter: } \alpha = \frac{\text{days}}{N} \qquad (14)$$

An example value for N may be in the range of 10 to 30 days.

Given these constraints, the transition coefficients $a_w$ and $b_w$ can be computed as follows:

Transition working coefficients (15)

$$b_w = b_r \cdot e^{-t_s \cdot (a_{PRESTEP} - \alpha \cdot a_{PRESTEP} + \alpha \cdot a_r)} \cdot e^{a_r \cdot t_s}$$

$$a_w = a_{PRESTEP} - \alpha \cdot a_{PRESTEP} + \alpha \cdot a_r$$

The density estimate during the N days of transition is calculated using the $a_w$ and $b_w$ coefficients in the exponential model for the long-term density given in equation (7). Once N days have elapsed from the time of the density step, these coefficients become equal to the coefficient of the current regression analysis and the system proceeds as described during the usual periods of slow density changes described above.

The present invention incorporates a graphical user interface (GUI) implemented as an embedded web server executing on one of the processor platforms of the controller, for example 109. The user browses the web pages provided by the embedded server over one of the communications links to retrieve information about the system being monitored and to configure the gas monitoring apparatus and processes.

Figure 13:
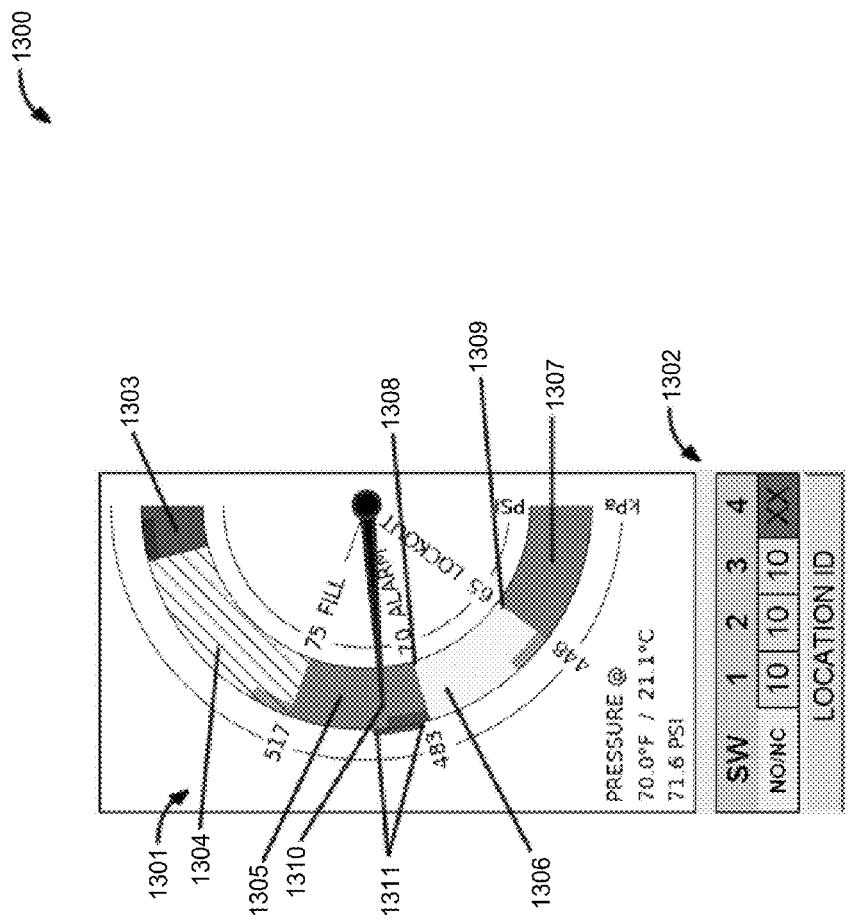
FIG. 13 is the Graphical User Interface (GUI) temperature corrected pressure gauge.

FIG. 13 shows the graphical temperature corrected pressure gauge 1300 that tracks short-term density 1301 in all embodiments and threshold switch contact states 1302 when present in particular embodiments. The gauge is demarcated into pressure regions corresponding to overpressure 1303, high operating range 1304, normal operating range 1305, alarm region 1306, and lockout region 1307. The switches when present are generally set to actuate when the temperature corrected pressure reaches the alarm threshold point 1308 or the lockout threshold point 1309. The graphical switch state indicators 1302 show whether a switch contacts normally open (NO) and normally closed (NC) are in the open state (value 0) or the closed state (value 1). Switches can be configured such that either the NO or the NC contact signals the threshold event. The example in FIG. 13 shows all NO contacts closed (1-state) and all NC contacts open (0-state). This state corresponds to no alarm condition and no lockout condition and correlates with the gauge needle 1310 comfortably positioned within the normal operating range 1305.

As described above, because of temperature disparities between the real-time sensor temperature $T_G$ and the effective gas temperature $T_{GAS}$, real time density and contact indications that respond to $T_G$ can vary significantly from actual gas density states that are determined by $T_{GAS}$. A feature of the graphical gauge 1300 is the overlay of the long-term density estimate onto the gauge 1311, the overlaid mark on the outer circumference of the gauge indicia. The span (circumferential length) of the mark is proportional to the density estimate confidence level. High confidence is represented by a very small span (small uncertainty). Longer spans represent lower confidence levels (larger uncertainty). For example, the size of the particular mark 1311 shown in the Fig. represents a 65% confidence level. Notice that the mark is offset somewhat from the pressure needle 1310 (the needle does not point exactly to the center of the mark 1311). This is because the breaker is at an early evening time where the gas temperature is 2-3 degrees warmer than the sensor temperature.

Figure 14:
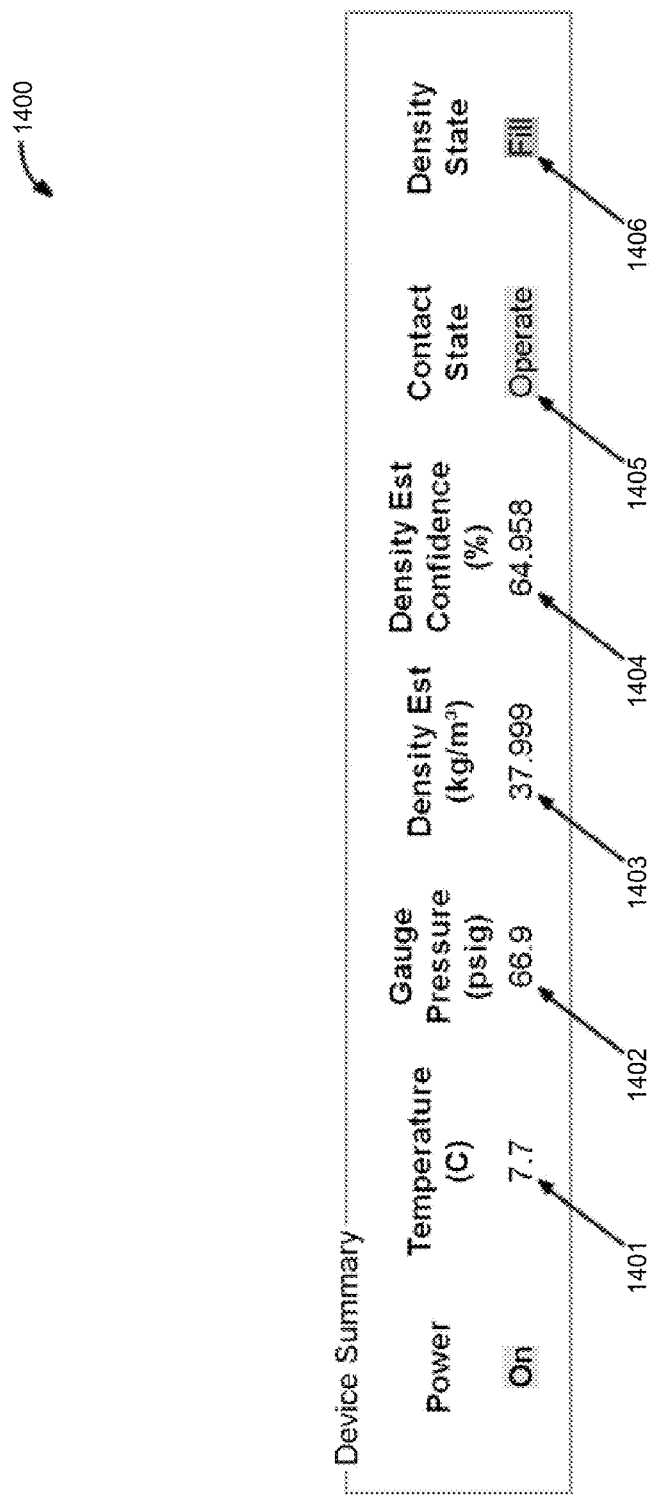
FIG. 14 is the GUI Device Summary panel.

The Device Summary panel 1400 is shown in FIG. 14 and conveys instantaneous conditions of sensor Temperature (C) 1401 and Gas Pressure (psig) 1402. The long term Density Est. (kg/m3) 1403 and Density Estimate Confidence (%) 1404 are also displayed. The interpretation of the switch Contact State 1405 is shown along with the interpretation of the Density State 1406 which is based upon the long term density estimate when available.

Figure 15:
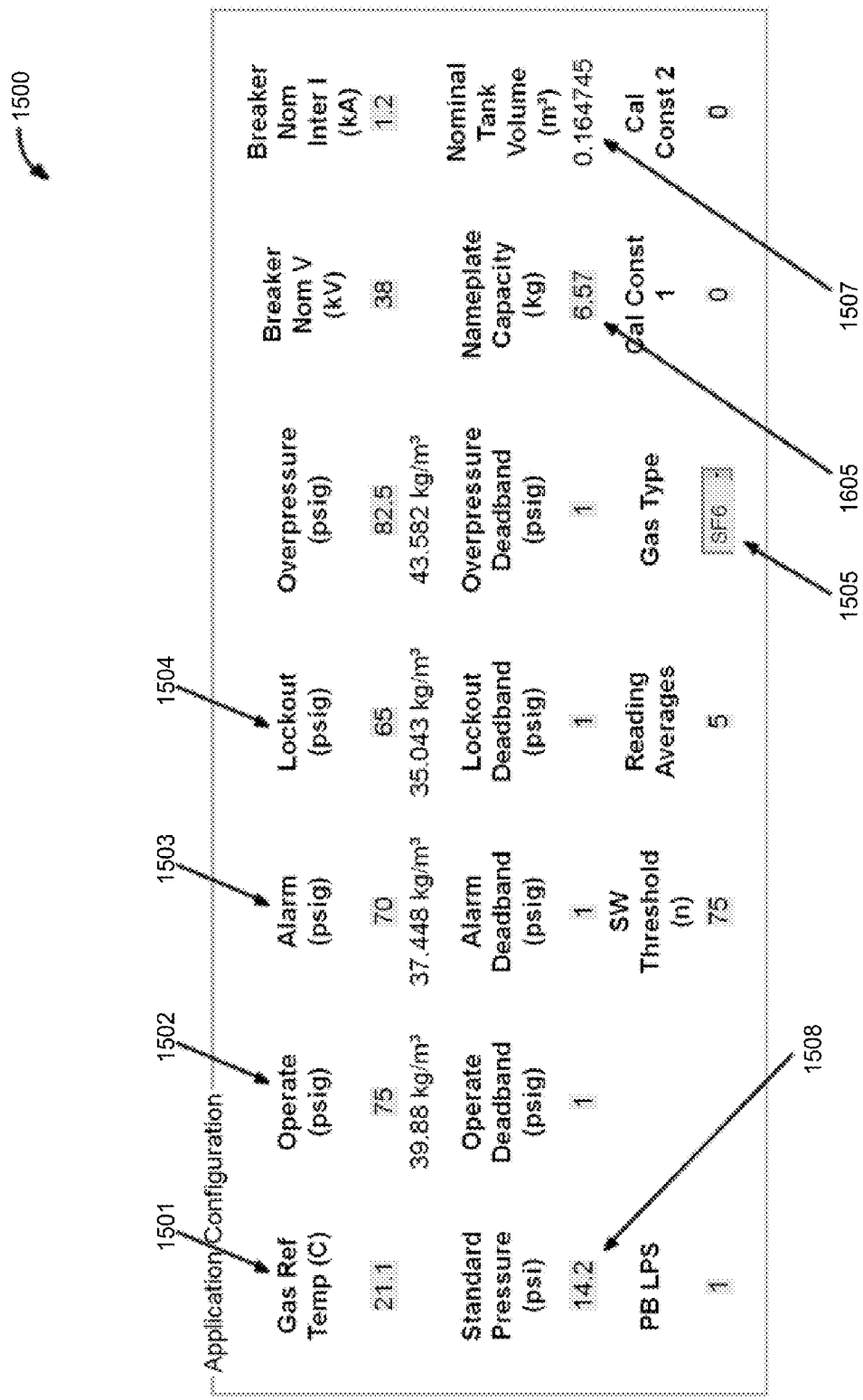
FIG. 15 is the GUI Application Configuration panel.
Figure 16:
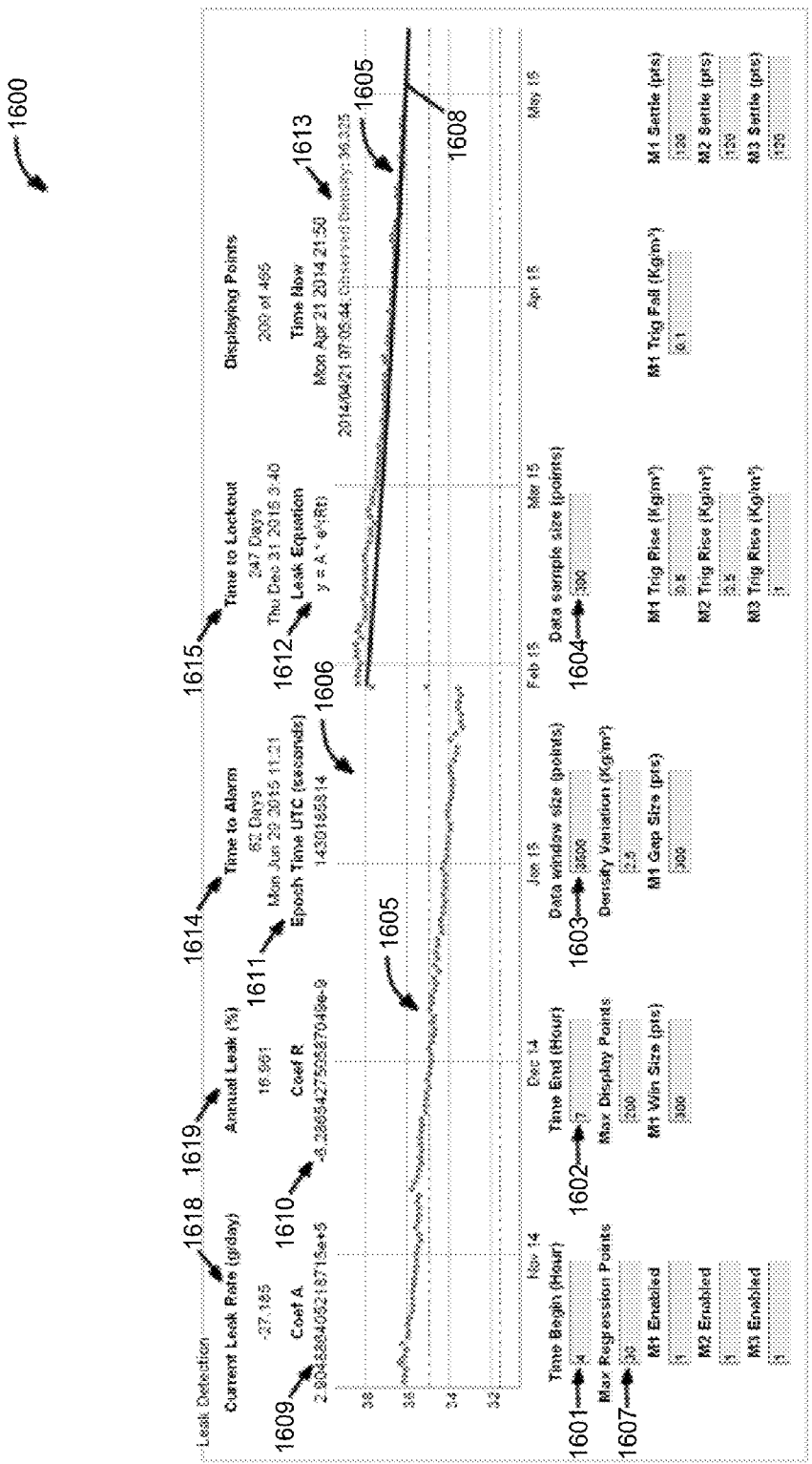
FIG. 16 is the GUI Leak Detection panel.

The Application Configuration panel 1500 of FIG. 15 allows the user to enter Gas Ref Temp 1501, Operate (psig) 1502, Alarm (psig) 1503, and Lockout (psig) 1504 pressures as well as to select the Gas Type 1505. The Nameplate Capacity (kg) 1506 can be entered and the Nominal Tank Volume (m$^3$) 1507 is calculated based upon the nameplate capacity, gas type, operate pressure, and reference temperature. Also, to properly interpret all of these parameters, in addition to Gas Ref Temp, a reference atmospheric pressure condition needs to be defined 1508. This can be entered by the user but defaults to standard pressure as defined by NIST and other standards organizations for gas systems, namely 14.696 psig The Leak Detection panel 1600 is shown in FIG. 16. Programmable parameters define a daily time range from Time Begin (Hour) $H_{BS}$ 1601 to Time End (Hour) $H_{ES}$ 1602 over which Data window size (points) $\Delta t_{RSMIN}$ 1603 regions are evaluated to find the region of maximum temperature stability from which Data sample size (points) $\Delta t_{SS}$ 1604 are then utilized to produce the representative diurnal density estimate each day.

These diurnal estimates are plotted as points $d_{RD}$(day), $t_{BEST}$ (day) 1605 on the graph 1606. The most recent Max Regression Points 1607 are utilized for exponential regression and the resulting trend line 1608 is shown on the graph along with the coefficients of regression Coef A 1609 and Coef R 1610. The independent variable is currently Epoch Time UTC (seconds) 1611 and this number marches forward one second at a time. The exponential equation is the long term density estimating equation 1612 corresponding to equation (7) above. It is used to compute the current density estimate 1613 as well as time to Alarm 1614 and Time to Lockout 1615 density levels. The previously defined Nameplate Capacity is used to estimate both Current Leak Rate (g/day) 1616 and the Annual Leak (%) 1617. Most organizations strive to meet EPA goals of an aggregate $SF_6$ loss rate of 1% of Nameplate Capacity or less.

Figure 17:
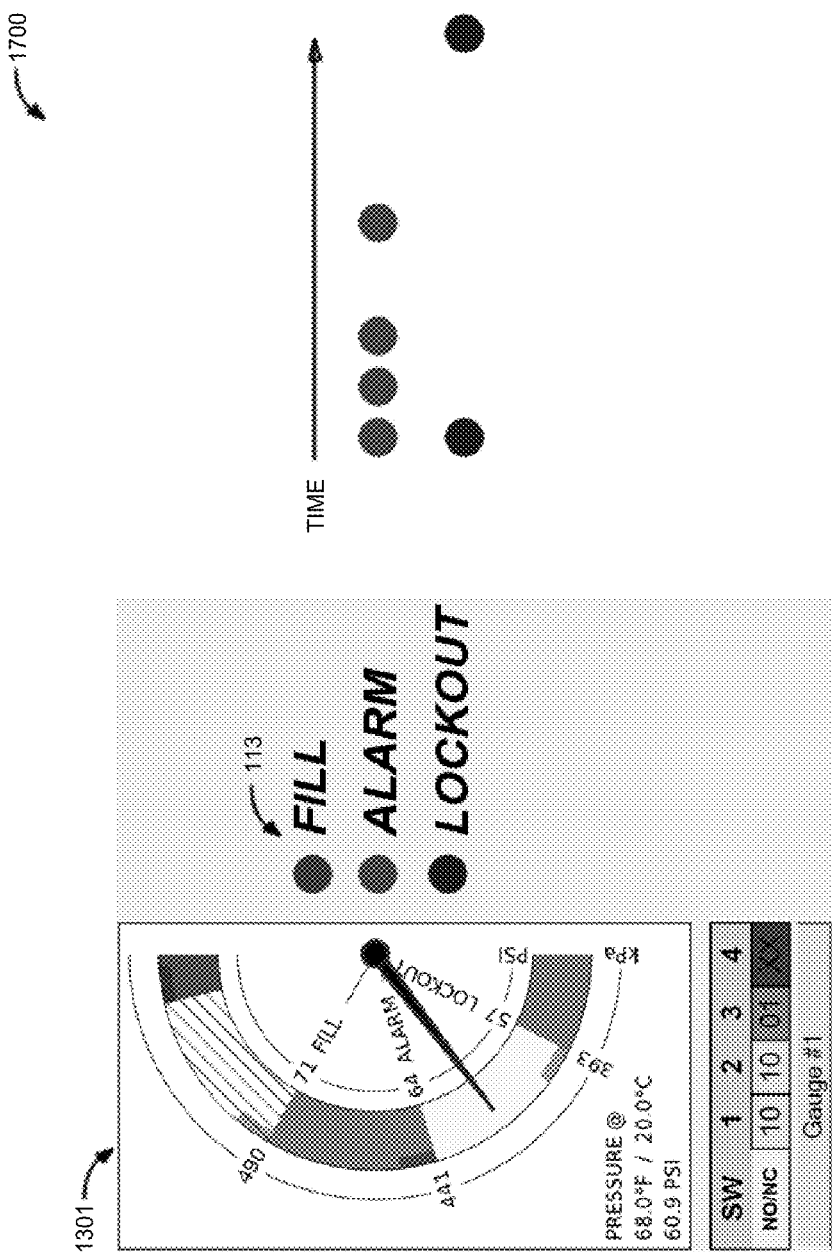
FIG. 17 shows the Fill, Alarm, and Lockout LED status indicators.

The present invention uses several LED indicators in a way that provides a high resolution (1 psi for example) indication of pressure even without the use of a bulky, costly gauge. FIG. 17 is an example of the LED signaling 1700 of the present invention. The graphical gauge 1301 that would be viewed via a web browser is shown next to a group of LEDs 113. The gauge is showing a pressure level below alarm level of approximately 60 to 61 psi. The user viewing the LEDs only without benefit of the gauge reaches the same conclusion given the following signal pattern: For each 1 psi below the alarm threshold, the controller flashes the ALARM LED once. To make these flashes easy to count, they are controlled in groups of up to (3) flashes with a pause before the next group. This is similar to Morse code characters dot-dot-dot-pause-dot . . . . This time based pattern of flashes is shown as 1702. Seeing 3+1 flashes tells the user that the current pressure is between 3 and 4 psi below the known alarm level of 64 psi, i.e. 60 to 61 psi. In addition, since the controller is aware that the density level has been decreasing over time, the next lower LED, the LOCKOUT LED, provides one quick flash at long intervals, depicted at 1703, communicating that a leak has been detected.

A primary objective of the present invention with respect to a gas in a tank being monitored is to measure differential and or absolute pressure accurately and to estimate the density with a high degree of accuracy using adaptive processing to eliminate variations that are simply artifacts of the application circumstances. Temperature disparities have been discussed as a major contributor to such artifacts and the processes supporting the long-term density estimation described herein minimize these temperature effects. Under system conditions where gas is either not leaking or only doing so very slowly, the long-term density estimator will also be changing very slowly as time progresses. To a high degree of accuracy therefore, over short time frames of several hours, the density may be considered to be practically constant. Temperature will vary significantly over these relatively short time frames, however. Taking advantage of these facts, at anytime, given an accurate pressure measurement and density estimate, the present invention uses the virial gas model of equation (3) to calculate the effective temperature of the gas having such a pressure and density. This process results in a measurement called the density inferred temperature $T_{DENSITY}$.

Because the virial model comprises a second order coefficient that depends in a non-linear way on temperature, a straight-forward method for calculating TD uses a simple iterative technique. An initial value for temperature $T_{GUESS}$ is guessed (for example the current $T_G$ value). $T_{GUESS}$ is plugged into equations (3a) and (3b) along with the other requisite variable and constant values to yield a density value. If the density value varies by more than a prescribed amount from the current density estimate $d_{LT}(t)$ that is believed to be accurate, the value of $T_{GUESS}$ is updated and a next iteration of evaluation is performed. The process completes when the last iteration yields a density value sufficiently close to $d_{LT}(t)$ at which point $T_{GUESS}$ is $T_{DENSITY}$ being sought.

Figure 18A:
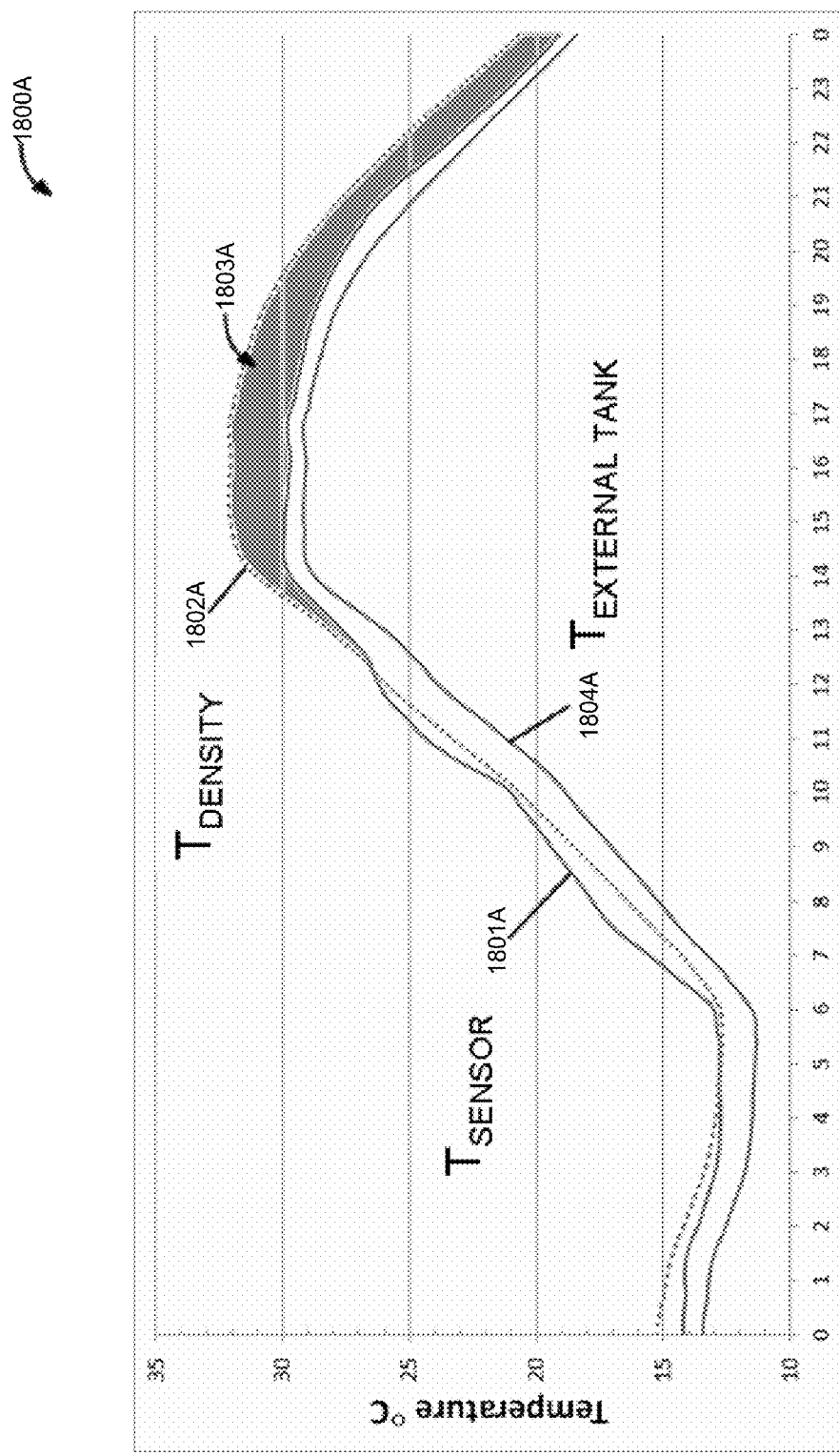
FIG. 18A shows measured and density inferred temperatures over the course of a day.

FIG. 18A is a graph 1800A depicting the relationships over the course of a day between sensor temperature $T_S$ 1801A, density inferred temperature $T_{DENSITY}$ 1802A, and an external measurement $T_{EXT}$ 1804A acquired from an independent sensor positioned carefully on the gas tank wall. The first thing to note is the divergence between $T_S$ and $T_{DENSITY}$ in $13^{th}$ through $24^{th}$ hour of the day, the disparity being labeled 1803A. This is deduced not to be a function of $T_S$ being inaccurate because $T_S$ tracks $T_{EXT}$ well (some rather constant offset) over the entire course of the day. What remains is the phenomenon that the effective gas temperature indicated by $T_{DENSITY}$ is for some reason higher than both $T_S$ and $T_{EXT}$ for a significant portion of the day.

Recalling that the gas being monitored is enclosed in high-voltage switchgear with high-current carrying contacts, the explanation for the unilateral rise in $T_{DENSITY}$ in afternoon hours rests on the $I^2R$ power dissipation in the contacts and conductors of the switchgear (where I is current and R is resistance) that heats the gas from within the tank. For the conditions described, $T_{DENSITY}$ is both a more accurate short-term measure of gas temperature and useful indicator of self-heating of gas within the tank which in turn is a useful indicator of contact resistance of the switchgear therefore state-of-repair of the equipment.

Figure 18B:
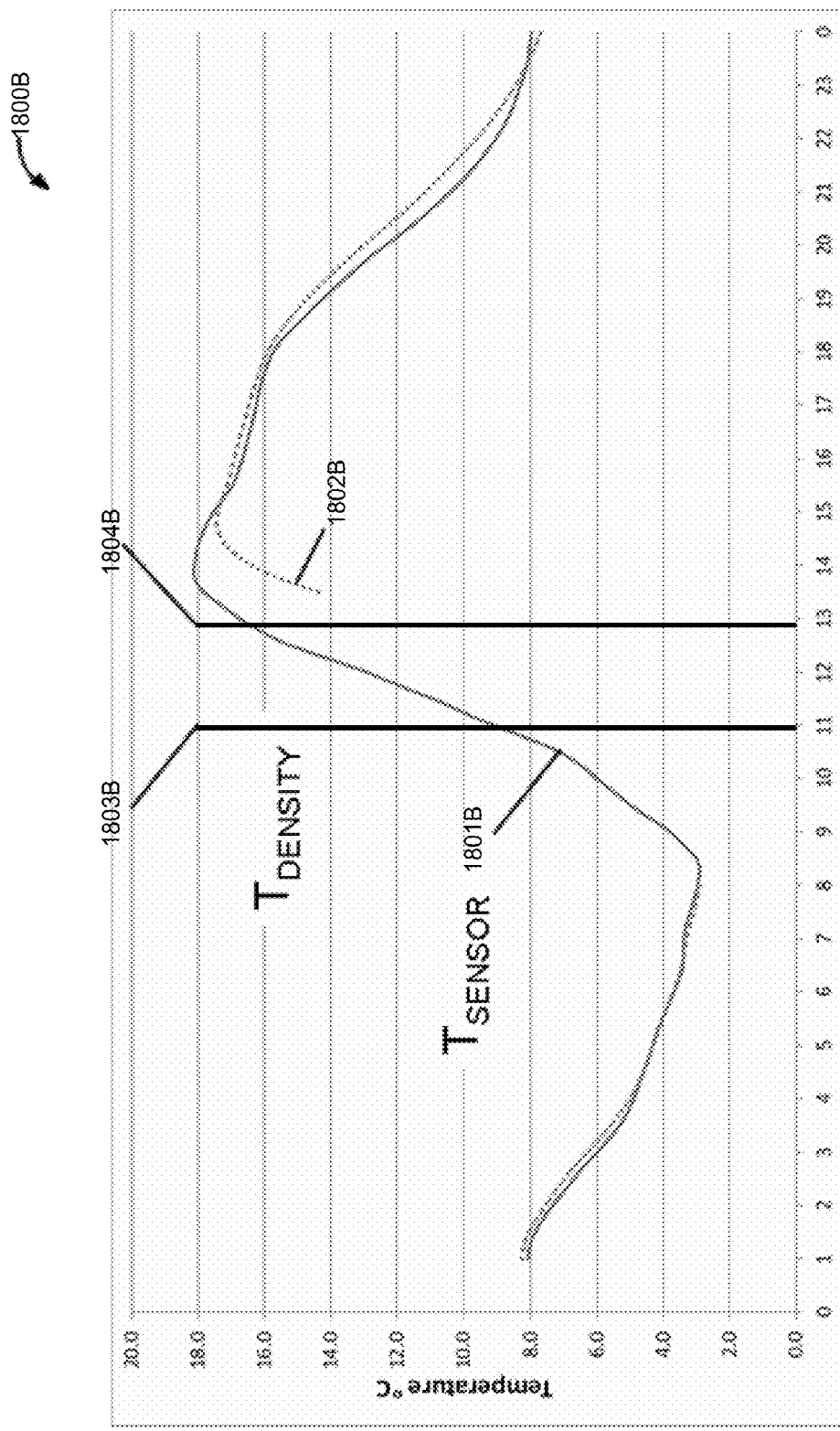
FIG. 18B shows density inferred temperatures associated with a no-current condition and gas fill.

FIG. 18B is a graph 1800B showing a day when the high-voltage breaker being monitored in the example of FIG. 18A is taken out of operation in the early afternoon at time 1803B to have its gas content "topped off". After having been inoperative (carrying no current) for several hours, as expected, $T_{DENSITY}$ is much lower than $T_S$. The new gas introduced is at a lower than ambient temperature and takes some time after 1804B to come to temperature equilibrium with the tank and system.

It is a known fact that a particular gas will change from the gaseous to the liquid state at particular combinations of higher pressure and lower temperature. This is simply called liquification. For each particular gas or gas mixture of interest, a family of points $P_{LIQ}$, $T_{LIQ}$ representing thresholds at which liquification begins for each particular gas are stored in the data store 210 and can be accessed by controller 209. A range of points covering the pressures and temperatures of interest in sufficient number to provide the desired resolution are stored. For each measurement of $T_G$ and $P_{GAS}$ for a given gas type the controller can check whether $P_{GAS}$ falls above or below $P_{LIQ}$ for $T_{LIQ}$ in close proximity to $T_G$. If $P_{GAS} > P_{LIQ}$, the controller notes a liquification warning event in the data store and communicates this warning to the user via the network connections and GUI.

The invention described herein has been set forth by way of example only. Those skilled in the art will readily recognize that changes may be made to the invention without departing from the spirit and scope of the invention as defined by the claims which are set forth below.

The invention claimed is:

1. A process for operating a gas monitoring apparatus to measure gas in a tank using sensors, controllers, and algorithms comprising the steps of:
   a controller acquires a gas pressure signal from a gas pressure sensor connected to the tank being monitored;
   said controller converts said gas pressure signal into a calibrated gas pressure value in engineering units of force per unit area;
   said controller acquires an atmospheric pressure signal from an atmospheric pressure sensor; said controller converts said atmospheric pressure signal into a calibrated atmospheric pressure value of atmospheric pressure in engineering units of force per unit area;
   said controller sums said calibrated gas pressure value and said calibrated atmospheric pressure value yielding a calibrated absolute gas pressure value;
   said controller acquires a gas temperature signal from a gas temperature sensor;
   said controller converts said gas temperature signal into a calibrated gas absolute temperature value in engineering units of absolute temperature;
   said controller uses a gas type received from an interface to lookup a virial coefficient model equation;
   said controller uses said virial coefficient model equation and said absolute gas temperature to calculate a second order virial coefficient;
   said controller uses said second order virial coefficient, said absolute gas pressure, said absolute gas temperature, a gas constant, and a virial equation to calculate a first gas density value;
   said controller repeats said above steps at a selected first measurement frequency developing a first time sequence of samples comprising said calibrated absolute gas pressure value, said calibrated absolute gas temperature value, and said first gas density value at each time separated by a first measurement time interval defined by the selected first measurement frequency.

2. The process for operating a gas monitoring apparatus to measure gas in a tank using sensors, controllers, and algorithms of claim 1 further comprising the steps of:
   receiving from the interface a beginning time-of-day corresponding multiple times within said first density time sequence separated by 24 hours;
   receiving from the interface an ending time-of-day corresponding multiple times within said first density time sequence separated by 24 hours, said ending time-of-day being later than said beginning-time-of day;
   receiving from the interface a first number of samples less than or equal to the number of samples in said first density time sequence between said beginning time-of-day and said ending-time of day inclusive;

receiving from the interface a second number of samples less than said first number of samples;

said controller calculates a root-mean-squared value of all first calibrated absolute temperature values from all samples of said first time sequence in a subset of samples starting with the sample most closely aligned in time with said beginning time-of-day and continuing for each subsequent sample until said first number of samples has been processed yielding a first RMS temperature value;

said controller calculates a root-mean-squared value of all calibrated absolute temperature values from all samples of said first time sequence in a subset of samples starting with a next subsequent sample and continuing for each subsequent sample until said first number of samples has been processed yielding a next RMS temperature value;

said controller repeats said previous step until the time of said next subsequent sample reaches or exceeds said ending time-of-day creating a first RMS temperature value sequence of samples comprising an RMS temperature value at said starting times separated by said first measurement time interval;

said controller selects the RMS temperature sample from said first RMS temperature sequence having the least RMS density value and the latest starting time defining a first flattest temperature region time;

said controller identifies a first representative subset of samples of said first time sequence containing said second number of samples from the latest samples of said first number of samples from said first flattest temperature region in time;

said controller calculates a first representative average calibrated absolute temperature value by averaging the calibrated absolute temperature value of each sample of said representative subset;

said controller calculates a first representative average calibrated absolute pressure value by averaging the calibrated absolute pressure values of each sample of said representative subset;

said controller uses said second order virial coefficient, said first representative absolute gas pressure, said first representative absolute gas temperature, a gas constant, and a virial equation to calculate a first representative gas density value, and said controller repeats said above steps at the rate of a second measurement time interval of developing a second time sequence of samples comprising said representative calibrated absolute gas pressure value, said representative calibrated absolute gas temperature value, and said representative gas density value at each time separated by said second measurement time interval.

3. The process for operating a gas monitoring apparatus to measure gas in a tank using sensors, controllers, and algorithms of claim 2 further comprising the steps of: receiving from the interface a third number of samples;

said controller identifies a subset of the latest samples of said second time sequence of samples containing said third number or less samples;

said controller selects a first function comprising first function parameters and calculates values for said first function parameters such that the value of the average of the squared differences of said first function values generated when said first function is evaluated with said first function parameters at each time of each sample of said second time sequence and the respective said representative gas density value of each respective sample is minimized, and said controller repeats said above steps at the rate of said second measurement time interval developing a third time sequence of samples comprising said first function parameter values, at each time separated by said second measurement time interval.

4. The process for operating a gas monitoring apparatus to measure gas in a tank using sensors, controllers, and algorithms of claim 3 further comprising the steps of:

receiving from the interface a first density threshold value, and said controller utilizes said first function with said first function parameter values of the latest sample of said third time sequence to calculate a first threshold attainment time at which said first function value is equal to said first density threshold value.

5. The process for operating a gas monitoring apparatus to measure gas in a tank using sensors, controllers, and algorithms of claim 4 further comprising the steps of:

the controller repeats said previous steps at the rate of said second measurement interval developing a fourth time sequence of samples comprising said first threshold attainment time at each time separated by said second measurement interval.

6. The process for operating a gas monitoring apparatus to measure gas in a tank using sensors, controllers, and algorithms of claim 1 further comprising the steps of:

said controller communicates said calibrated gas pressure value, said calibrated absolute temperature value, and said first gas density value to the interface.

7. The process for operating a gas monitoring apparatus to measure gas in a tank using sensors, controllers, and algorithms of claim 3 further comprising the steps of:

receiving from the interface a first density threshold value, and said controller utilizes said first function with said first function parameter values of the latest sample of said third time sequence to calculate a long-term instantaneous density estimate at the present time;

said controller compares said first density threshold value to said long-term instantaneous density estimate, and said controller communicates to said interface the result of the step of the controller comparing said first density threshold value to said long-term instantaneous density estimate.

* * * * *